US008410456B2

(12) United States Patent
Yamamoto et al.

(10) Patent No.: US 8,410,456 B2
(45) Date of Patent: Apr. 2, 2013

(54) MEASUREMENT DATA CORRECTION METHOD, OPTICAL TOMOGRAPHY MEASUREMENT DEVICE AND STORAGE MEDIUM STORED WITH PROGRAM

(75) Inventors: Hiroaki Yamamoto, Ashigarakami-gun (JP); Yu Tojo, Ashigarakami-gun (JP); Hitoshi Shimizu, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 268 days.

(21) Appl. No.: 12/886,985

(22) Filed: Sep. 21, 2010

(65) Prior Publication Data
US 2011/0077888 A1 Mar. 31, 2011

(30) Foreign Application Priority Data
Sep. 25, 2009 (JP) ................................. 2009-220931

(51) Int. Cl.
*G01J 1/58* (2006.01)
(52) U.S. Cl. ................. 250/459.1; 250/252.1; 250/458.1
(58) Field of Classification Search .................. 250/458.1
See application file for complete search history.

(56) References Cited

U.S. PATENT DOCUMENTS

| 7,212,848 B1* | 5/2007 | Wake et al ...................... 600/476 |
| 2004/0015062 A1* | 1/2004 | Ntziachristos et al. ........ 600/312 |
| 2008/0219933 A1* | 9/2008 | Ntziachristos et al. ........ 424/9.6 |
| 2009/0153850 A1* | 6/2009 | Nielsen et al. ............. 356/243.1 |

FOREIGN PATENT DOCUMENTS

| JP | 2004-125605 A | 4/2004 |
| JP | 2008-051773 A | 3/2008 |

* cited by examiner

*Primary Examiner* — David Porta
*Assistant Examiner* — Marcus Taningco
(74) *Attorney, Agent, or Firm* — Sughrue Mion, PLLC

(57) ABSTRACT

A measurement data correction method is provided. A living organism is employed as a test sample, fluorescent light generated by excitation light from a fluorescent substance administered to the test sample is received by a light receiving component at a plurality of locations around the periphery of the test sample in a flat plane passing through an observation site of the test sample, and the method is employed for reconstruction of an optical tomographic image of the test sample along the flat plane passing through the observation site. The method includes: generating corrected measurement data, as measurement data to be used in reconstruction of an optical tomographic image along the flat plane passing through the observation site of the test sample, from an obtained first measurement data and an obtained first standardization measurement data using a defined correction coefficient.

12 Claims, 16 Drawing Sheets

MEASUREMENT DATA CORRECTION METHOD, OPTICAL TOMOGRAPHY MEASUREMENT DEVICE AND STORAGE MEDIUM STORED WITH PROGRAM

CROSS-REFERENCE TO RELATED APPLICATION

This application claims priority under 35 USC 119 from Japanese Patent Application No. 2009-220931 filed on Sep. 25, 2009, the disclosure of which is incorporated by reference herein.

BACKGROUND OF THE INVENTION

1. Field of the Invention

The present invention relates to a measurement data correction method applied in optical tomography for generating optical tomographic images with a measurement subject of a body tissue or the like, and to an optical tomography measurement device and a storage medium stored with a program.

2. Description of the Related Art

Body tissue has transmissivity to light of a specific wavelength, such as, for example, near infrared radiation. Therefore, in the field of pathology, for example, a fluorescent substance is administered to a living organism, fluorescent light generated from the administered fluorescent substance is measured two-dimensionally, and regenerated as a visible image (tomographic image) of, for example, the distribution state of the fluorescent substance in the body tissue.

Various image processing is performed in order to regenerate a correct image from measurement data. For example, in Japanese Patent Application Laid-Open (JP-A) No. 2004-125605 generation of image data at evenly spaced intervals by subjecting one-dimensional image data to interpolation, so as to regenerate a two-dimensional image, is proposed.

Further, in JP-A No. 2008-51773 regeneration of an image without density unevenness by storing shading data, and correcting image data obtained by measurement using the shading data, is proposed.

However, light of a specific wavelength, such as near infrared radiation or the like, propagates within a living organism while scattering isotropically. Therefore, in experimental fields such as pathology, using living organism such as small animals as the measurement subject, a fluorescent substance is joined to an antibody that specifically attaches to a lesion site, such as a tumor site or the like, and then administered to the measurement subject. Then, there is a proposal, in optical tomography using fluorescent light, to generate fluorescent light from the fluorescent substance by illuminating excitation light from the exterior of the measurement subject, receiving the light, and generating tomographic images in which the distribution of the fluorescent substance is regenerated (reconstructed) from the received fluorescent light.

By so doing, lesion sites within the measurement subject can be made clearly visible from the reconstructed optical tomographic images.

In fluorescent optical tomography, excitation light is illuminated towards a single point on the surface of a living organism, and fluorescent light generated from the fluorescent substance within the living organism by the excitation light and emitted externally is measured in plural locations in the same flat plane (measurement plane). In a case in which this is performed, while moving the illumination position of the excitation light around the periphery of the living organism, the position and density of the fluorescent substance is computed using measurement data obtained by measuring the fluorescent light at each of the respective illumination positions. By so doing, a two dimensional tomographic image is generated representing the density distribution of fluorescent substance (fluorescent light), sectioned on the measurement plane.

However, while illuminating excitation light towards the measurement subject and receiving the fluorescent light issuing from the measurement subject, not only is fluorescent light generated from the fluorescent substance received, but also various types of unwanted light, such as from reflected light of the excitation light and the like, are received, and data of this unwanted light is included within measurement data. This unwanted light prevents appropriate reconstruction of optical tomographic images.

SUMMARY OF THE INVENTION

The present invention is made in consideration of the above circumstances, and an object thereof is to provide, in fluorescent optical tomography, a measurement data correction method enabling reconstruction of appropriate optical tomographic images from which an unwanted light component has been removed from measurement data obtained by receiving light with a light receiving component, and to a optical tomography measurement device and storage medium stored with a program.

In order to achieve the above object, in a case in whic a living organism is employed as a test sample and fluorescent light generated by excitation light from a fluorescent substance administered to the test sample is received by a light receiving component at plural locations around the periphery of the test sample in a flat plane passing through an observation site of the test sample, a measurement data correction method of the present invention is employed for reconstruction of an optical tomographic image of the test sample along the flat plane passing through the observation site. The measurement data correction method includes: acquiring first measurement data that is measurement data in a flat plane passing through the observation site and acquiring second measurement data that is measurement data in a flat plane passing through a site of interest of the test sample different from the observation site; using a predetermined standardization sample for the test sample to acquire first standardization measurement data that is measurement data in a flat plane corresponding to the flat plane of the observation site, and to acquire second standardization measurement data that is measurement data corresponding to a flat plane of the site of interest; using the second measurement data and the second standardization measurement data corresponding to the site of interest of the test sample, and setting a correction coefficient such that the second standardization measurement data is cancelled out by the second measurement data; and generating corrected measurement data, as measurement data to be used in reconstruction of an optical tomographic image along the flat plane passing through the observation site of the test sample, from the first measurement data and the first standardization measurement data using the correction coefficient.

Further, for a living organism employed as a test sample with fluorescent light being generated by excitation light from a fluorescent substance administered to the test sample, an optical tomography measurement device of the present invention performs reconstruction, from measurement data obtained from receiving light with a light receiving component at plural locations around the periphery of the test sample in a flat plane passing through an observation site of the test sample, of an optical tomographic image of the test sample along the flat plane passing through the observation site. The device includes: a first acquiring component that acquires with the light receiving component first measurement data that is measurement data in a flat plane passing through the observation site and second measurement data that is measurement data in a flat plane passing through a site of interest of the test sample different from the observation site; a second acquiring component that uses a predetermined standardization sample for the test sample to acquire with the light receiving component first standardization measurement data that is measurement data in a flat plane corresponding to the flat plane including the observation site, and to acquire second standardization measurement data that is measurement data corresponding to a flat plane including the site of interest; a correction coefficient setting component that uses the second measurement data and the second standardization measurement data corresponding to the site of interest of the test sample, and sets a correction coefficient such that the second standardization measurement data is cancelled out by the second measurement data; and a correction component that generates corrected measurement data, of measurement data to be used in reconstruction of an optical tomographic image along the flat plane passing through the observation site of the test sample, from the first measurement data and the first standardization measurement data using the correction coefficient.

Furthermore, for a living organism employed as a test sample with fluorescent light being generated by excitation light from a fluorescent substance administered to the test sample, a storage medium readable by a computer of the present invention is a storage medium storing a program of instructions executable by the computer, functioning the computer as components, the computer provided to an optical tomography measurement device performing reconstruction, from measurement data obtained by a light receiving component receiving light at plural locations around the periphery of the test sample in a flat plane passing through an observation site of the test sample, of an optical tomographic image of the test sample along the flat plane passing through the observation site. The components includes: a first acquiring component that acquires with the light receiving component first measurement data that is measurement data in a flat plane passing through the observation site and second measurement data that is measurement data in a flat plane passing through a site of interest of the test sample different from the observation site; a second acquiring component that uses a predetermined standardization sample for the test sample to acquire with the light receiving component first standardization measurement data that is measurement data in a flat plane corresponding to the flat plane including the observation site, and second standardization measurement data that is measurement data corresponding to a flat plane including the site of interest; a correction coefficient setting component that uses the second measurement data and the second standardization measurement data corresponding to the site of interest of the test sample, and sets a correction coefficient such that the second standardization measurement data is cancelled out by the second measurement data; and a correction component that generates corrected measurement data, of measurement data to be used in reconstruction of an optical tomographic image along the flat plane passing through the observation site of the test sample, from the first measurement data and the first standardization measurement data using the correction coefficient.

BRIEF DESCRIPTION OF THE DRAWINGS

Exemplary embodiments of the present invention will be described in detail based on the following figures, wherein.

DETAILED DESCRIPTION OF THE INVENTION

Figure 1:
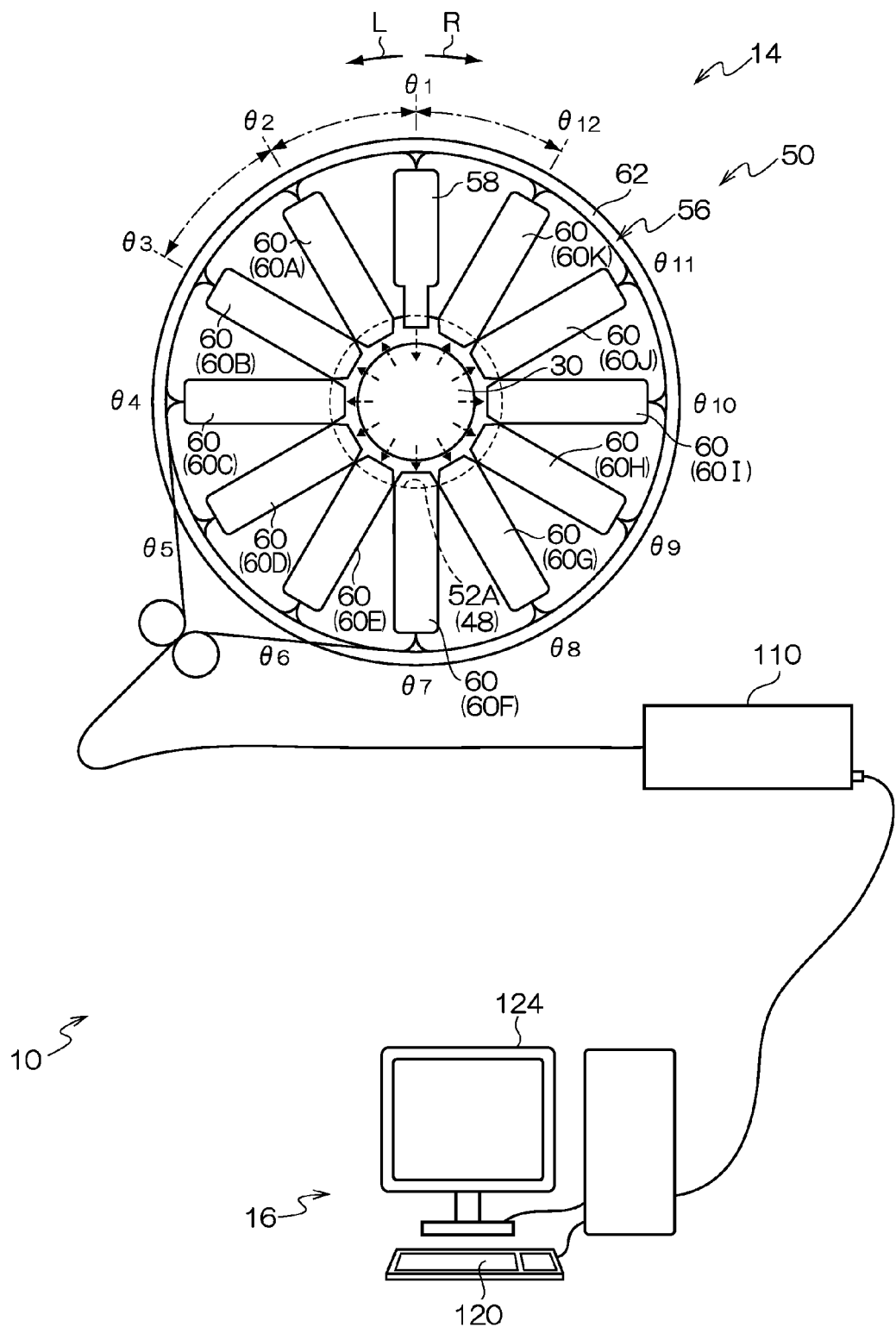
FIG. 1 is a configuration diagram of relevant portions of an optical tomography measurement system according to a present exemplary embodiment.
Figure 2:
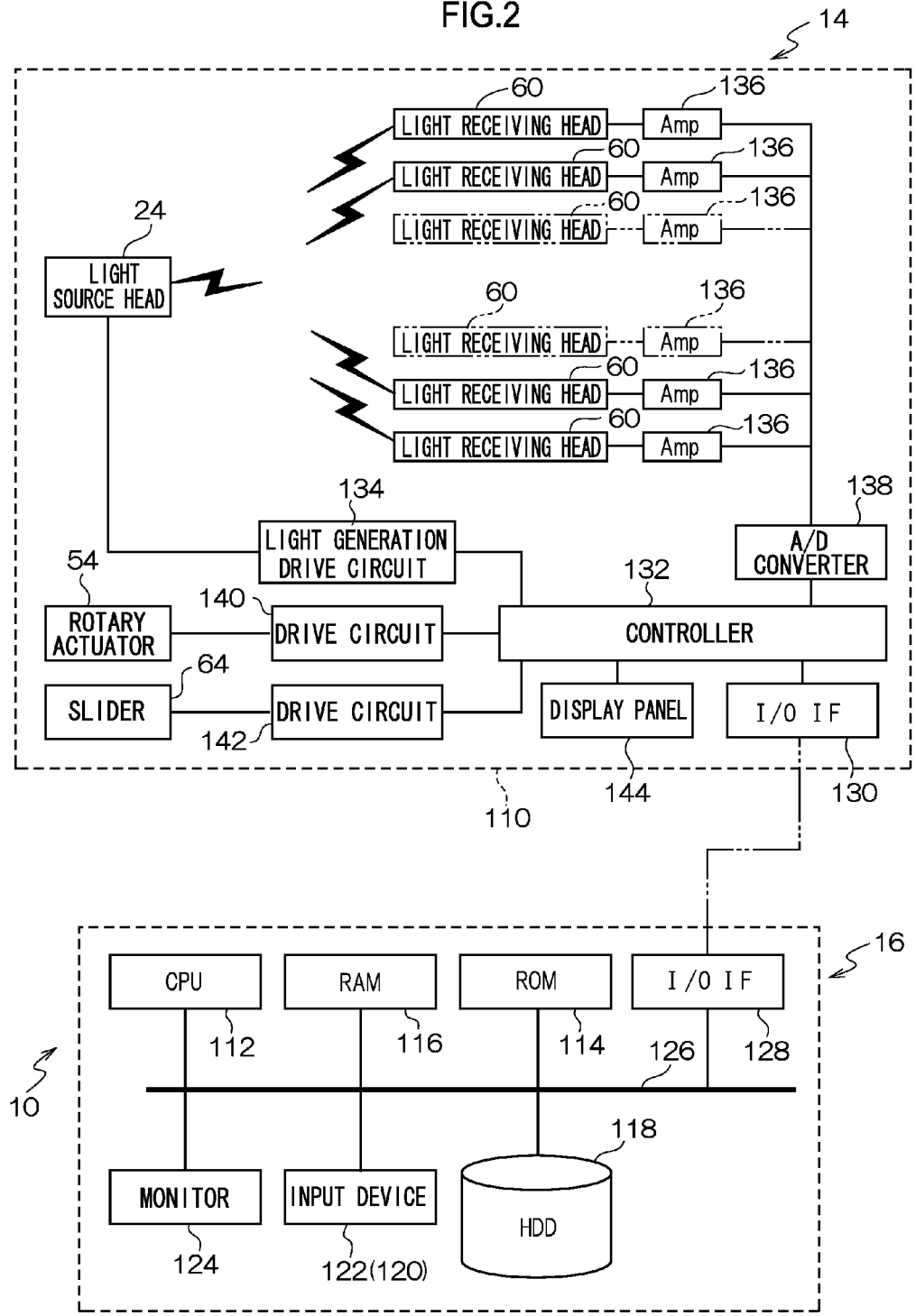
FIG. 2 is a schematic configuration diagram showing relevant portions of a control section of an optical measurement device and a data processing device.

Explanation follows of exemplary embodiments of the present invention, with reference to the drawings. FIG. 1 and FIG. 2 show an outline configuration of an optical tomography measurement system 10 according to the present exemplary embodiment. The optical tomography measurement system 10 has as the measurement subject, for example, a living organism, such as a nude mouse or the like, and generates a tomographic image showing the density distribution within the body of a fluorescent substance administered to the measurement subject (reconstructs an optical tomographic image). Explanation follows of a case with a mouse 12 as the measurement subject (see FIG. 5), in which reconstruction of an optical tomographic image of the mouse 12 is performed.

Figure 3:
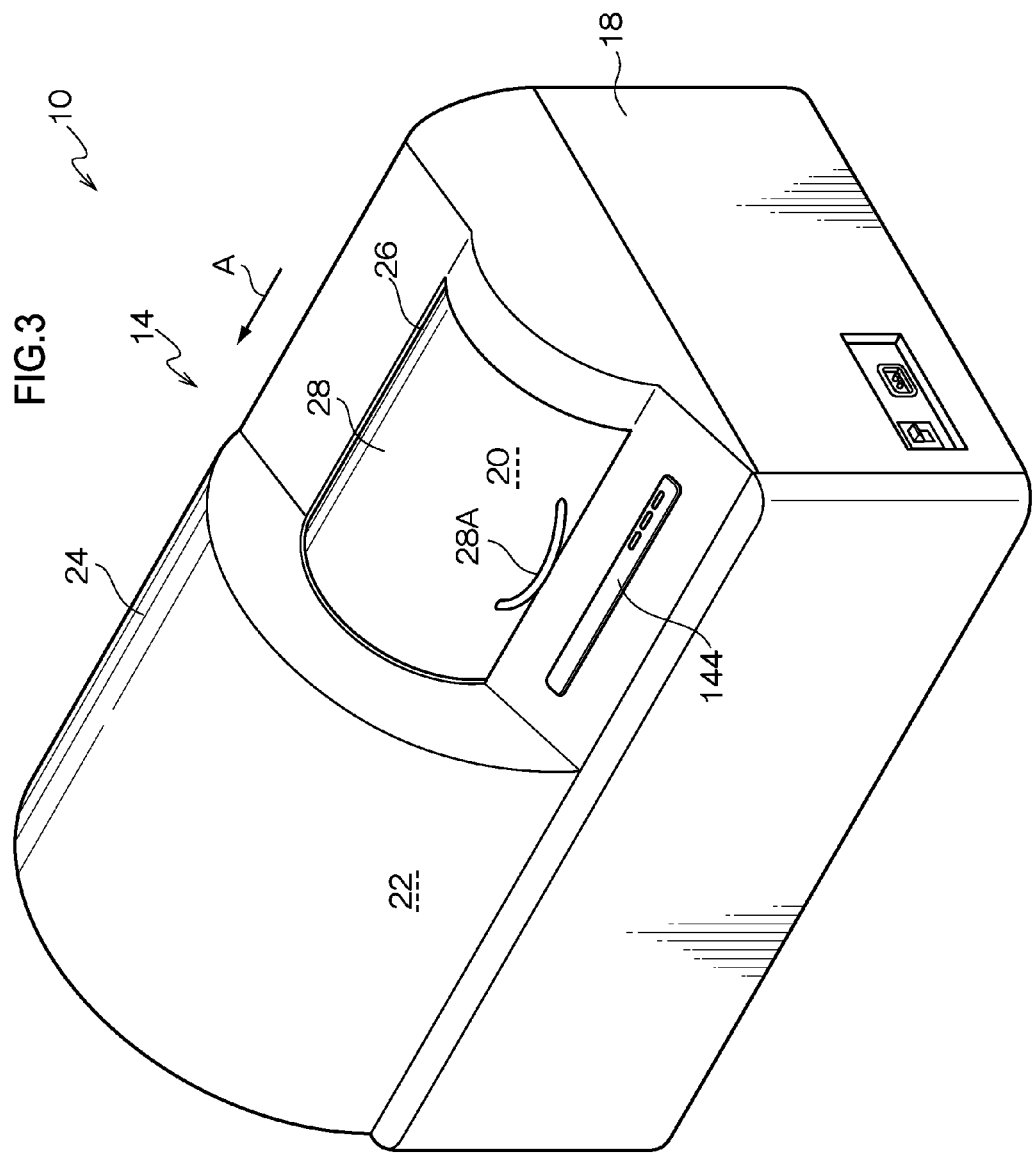
FIG. 3 is a perspective view showing the external appearance of an optical measurement device.

The optical tomography measurement system 10 is configured including an optical measurement device 14 and a data processing device 16. As shown in FIG. 3, the optical measurement device 14 is equipped with a case 18, formed in a substantially rectangular box shape. A loading section 20, into which a mouse 12 is loaded, and a measurement section 22, where fluorescent light generated from the loaded mouse 12 is measured, are provided within the case 18. Explanation is given below with the nearside in FIG. 3 and FIG. 4 referred to as the front face of the optical measurement device 14 (the device nearside), and the far side therein referred so as the far side.

Figure 4:
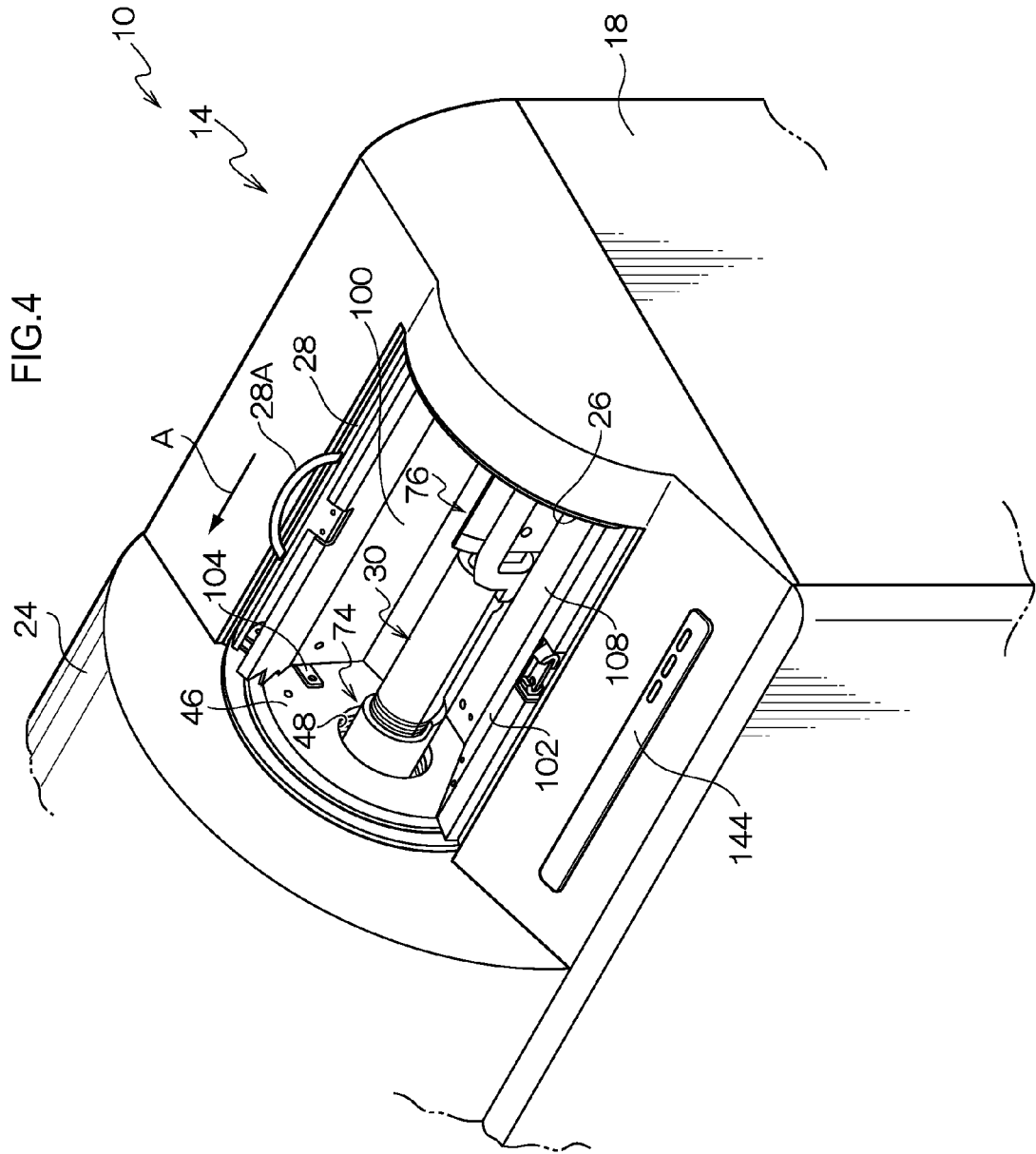
FIG. 4 is a perspective view of relevant portions of the optical measurement device of FIG. 3, showing an open state of a sliding door.

The top face (the face at the top side in FIG. 3) of the case 18 is provided with a cover 24 formed in a circular arc shape so as to form an upwards facing convex shape. The loading section 20 forms one end of the optical measurement device 14, in the axial direction of the circular arc of the cover 24, and the measurement section 22 forms the other end thereof. As shown in FIG. 4, a loading aperture 26 is formed as a rectangular shape in plan view at the loading section 20 side of the cover 24, and a sliding door 28 is provided to the loading aperture 26.

In the optical measurement device 14, for example, the loading aperture 26 is opened by gripping a handle 28A, and moving the sliding door 28 in a circumferential direction along a circular arc. Light to the inside of the case 18 is blocked by closing the loading aperture 26 with the sliding door 28.

Figure 5:
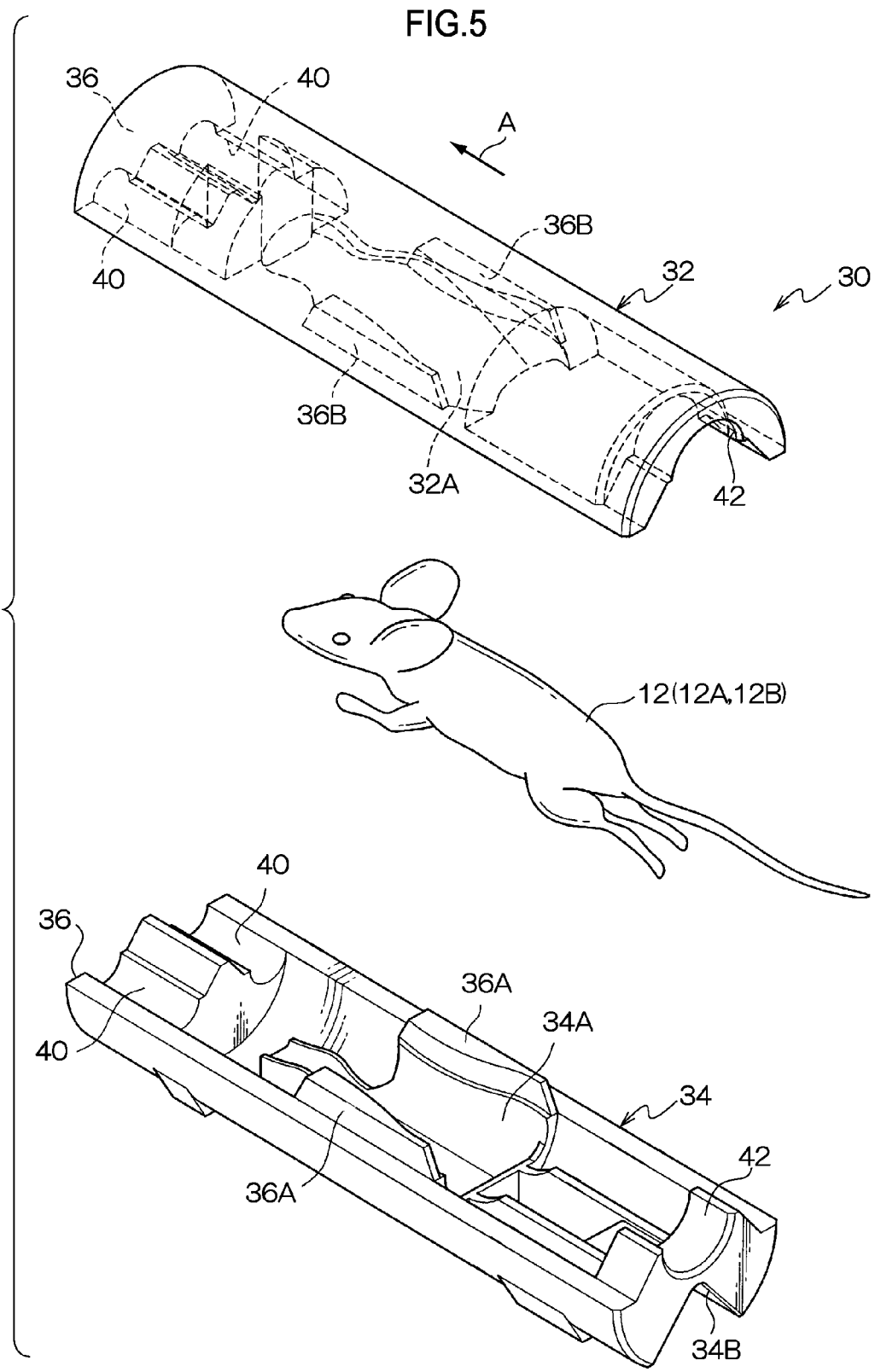
FIG. 5 is an outline perspective view showing a sample holder and a mouse.

As shown in FIG. 4, a sample holder 30 is employed in the optical measurement device 14, in a case of loading the mouse 12. As shown in FIG. 5, the sample holder 30 is configured from an upper mold block 32 and a lower mold block 34, so as to form a substantially circular column shape of a specific outer diameter, by superimposing and fitting the upper mold block 32 and the lower mold block 34 together.

The mouse 12 is accommodated in the sample holder 30 disposed with its body length direction along the axial direction of the sample holder 30, and a recess portion 32A and a recess portion 34A are formed to the upper mold block 32 and the lower mold block 34, respectively, so as to match the body shape of the mouse 12 to be accommodated. A pair of engagement protrusions 36A is formed to the lower mold block 34, and engagement recess portions 36B are formed in the upper mold block 32 corresponding to the engagement protrusions 36A.

The sample holder 30 accommodates the mouse 12 in the recess portion 34A by placing the mouse 12 in the lower mold block 34. In a case in which this is performed, the chest region to the lumber region of the mouse 12, this being the measurement site thereof, is restrained by the pair of engagement protrusions 36A, preventing epidermis from sticking out from the top of the recess portion 34A.

In the sample holder 30, in this state, the upper mold block 32 is superimposed on the lower mold block 34. In a case in which this is done, the engagement protrusions 36A of the lower mold block 34 fit into the engagement recess portions 36B of the upper mold block 32, and the mouse 12 is accommodated in such a state that its epidermis is in close contact with the inner face of the recess portion 32A of the upper mold block 32 and the recess portion 34A of the lower mold block 34.

Further, the end face of the sample holder 30 at the head end of the mouse 12 configures a reference surface 36, such that in a case in which the mouse 12 is accommodated in the sample holder 30, the position is determined relative to the reference surface 36 of each of organ according to the body shape (size). In the following explanation, the reference surface 36 side is referred to as the leading end side (leading end portion) of the sample holder 30, and the opposite side to that of the reference surface 36 is referred to as the rear end side (rear end portion). Further, in the optical measurement device 14 the sample holder 30 is moved along the axial direction, which is the length direction of the mouse 12, so as to be fed out from the loading section 20 into the measurement section 22, and this direction is shown below as the arrow A direction.

In the present exemplary embodiment, the mouse 12 is accommodated in the sample holder 30 in an anesthetized state (a still alive state), and air holes 40 are formed in the sample holder 30 at what will be the head end side of the mouse 12, enabling the mouse 12 accommodated within the sample holder 30 to breath.

A through hole 42 is formed in the sample holder 30 at the lower body side of the mouse 12 (the opposite side to that of the head), such that the tail of the mouse 12 is able to protrude out from the sample holder 30, and such that any defecation from the mouse 12 is dischargeable out from within the sample holder 30. Due thereto, even if the mouse 12 accommodated in the sample holder 30 defecates, such defecation is prevented from building up within the sample holder 30. Note that a waste outlet for defecation may be provided in the lower mold block 34, separate to the through hole 42.

Generally, a living organism, such as, for example, a mouse 12 or the like, acts as an anisotropic scattering medium to light. In an anisotropic scattering medium, forward scatter dominates in a region in which incident light that does not exceed a light penetration wavelength (equivalent scattering wavelength), however light scattering becomes isotropic in a region exceeding the light penetration wavelength (equivalent scattering wavelength), (an isotropic scatting region). In this isotropic scatting region, multiple scattering (isotropic scatting) of light occurs with random polarity.

Further, in a case in which anisotropic scattering media are in contact with each other, in a case in which light propagating by repeated isotropic scattering in one of the anisotropic scattering media enters the other anisotropic scattering medium, isotropic scattering continues without forward scattering occurring.

Furthermore, in a case in which light propagates in a high density medium while being subject to scattering, the distribution of light intensity may be represented by a light (photon) transport equation, which is a fundamental equation for describing the energy flow of a photon. However, scattering within the mouse 12 accommodated in the sample holder 30 can be treated as being in an isotropic scatting region in practice, and scattering of light in the mouse 12 can be approximated to isotropic scattering.

Thereby, the light intensity distribution can be represented using a diffusion equation, and in the data processing device 16, described below, the density distribution of light (fluorescent light) is obtained by computation to solve a diffusion equation employing the measurement results of the optical measurement device 14.

The sample holder 30 (the upper mold block 32 and the lower mold block 34) are formed using a substance that is an anisotropic scattering medium, in order that the accommodated mouse 12 can be treated as an isotropic scatting region in practice. In the present exemplary embodiment, a polyacetal resin (POM) with light transmission scattering coefficient $\mu'$ of $0.002 \text{ m}^{-1}$ to $0.1 \text{ m}^{-1}$ is employed as the substance of the sample holder 30. Note that the substance for forming the sample holder 30 is not limited thereto, and any substance may be appropriately used as long as it is an anisotropic scattering medium.

Figure 6A:
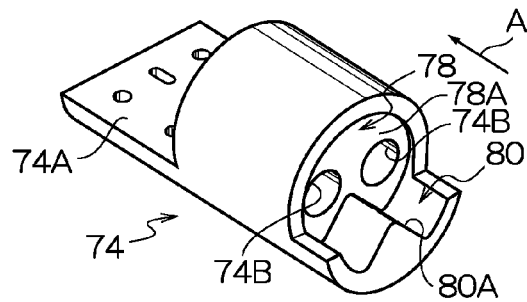
FIG. 6A is an outline perspective view showing a leading end bracket for supporting one end of a sample holder.
Figure 6B:
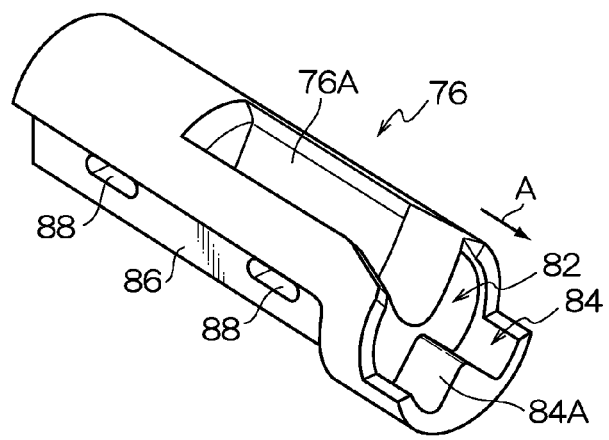
FIG. 6B is an outline perspective view showing a rear end bracket for supporting the other end of a sample holder.
Figure 6C:
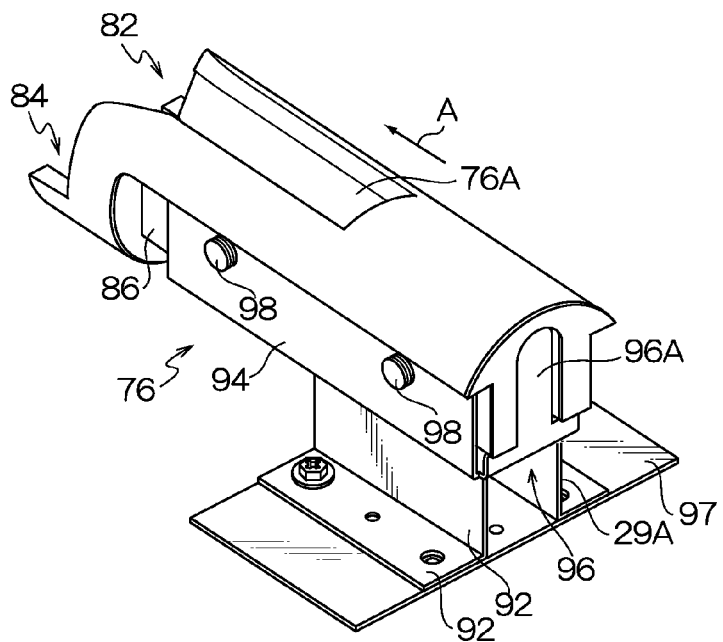
FIG. 6C is an outline perspective view showing attachment of the rear end bracket of FIG. 6B, as viewed from another direction.
Figure 7:
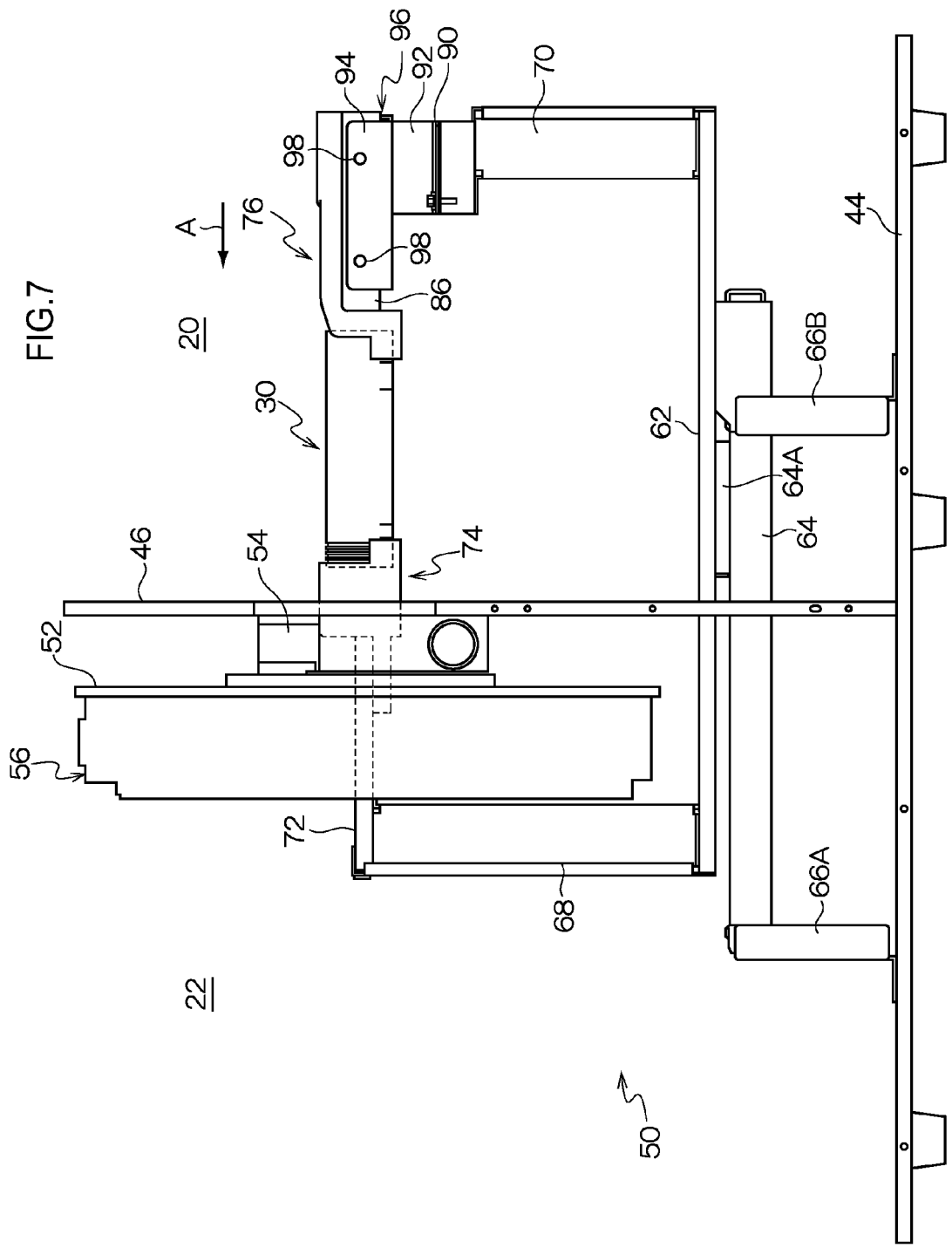
FIG. 7 is a schematic diagram of a measurement unit of an optical measurement device, as viewed from the front face side.
Figure 8:
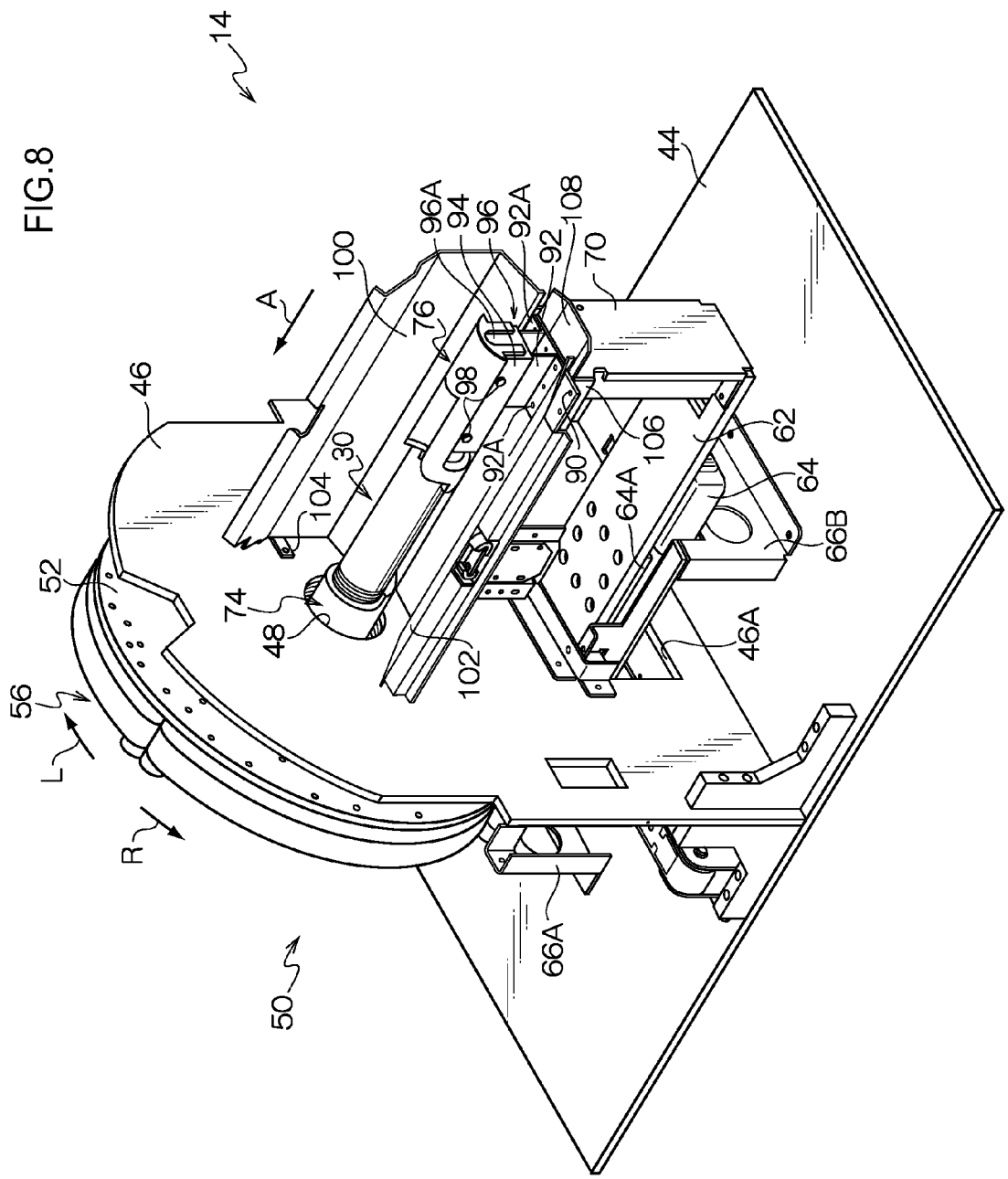
FIG. 8 is a schematic perspective view of a measurement unit, as viewed from a loading section side.

As shown in FIG. 7 and FIG. 8, a base plate 44 is provided to the optical measurement device 14. The base plate 44 is provided at a bottom portion within the case 18 (omitted from illustration in FIG. 6A to FIG. 6C, and FIG. 7). A separator 46 is provided standing up from the base plate 44. Due thereto, as shown in FIG. 4, in the optical measurement device 14, the inside of the case 18 is partitioned into the loading section 20 and the measurement section 22, and even in a case in which the loading aperture 26 is in an open state, incident light is suppressed to the measurement section 22 from the loading aperture 26.

As shown in FIG. 8, a through hole 48 is formed in the separator 46. In the optical measurement device 14, the sample holder 30 loaded into the loading section 20 moves in the arrow A direction, and is inserted from the leading end side, through the through hole 48, fed into the measurement section 22, and measurement processing is performed on the mouse 12 accommodated in the sample holder 30. Further, in the optical measurement device 14, in a case in which measurement processing is completed, the sample holder 30 is returned from the through hole 48 into the loading section 20.

As shown in FIG. 7 and FIG. 8, a measurement unit 50 is provided on the base plate 44 in the optical measurement device 14. The measurement unit 50 is equipped with a circular plate shaped head base 52. The head base 52 is disposed adjacent to the separator 46 on the measurement section 22 side, and a through hole 52A (see FIG. 1) is formed in an axial portion of the head base 52, coaxial to the through hole 48 of the separator 46.

As shown in FIG. 7, a rotary actuator 54 is disposed between the separator 46 and the head base 52. The rotary actuator 54 is formed with a through hole, not shown in the figures, that faces the through hole 48 of the separator 46, and the rotary actuator 54 is attached to the separator 46 such that this through hole is coaxial to the through hole 48.

The peripheral edge portion of the through hole configures a rotating portion of the rotary actuator 54, rotating around the circumferential direction of the through hole, and the head base 52 is attached to the rotating portion of the rotary actuator 54. Due thereto, the head base 52 is supported by the separator 46 via the rotary actuator 54, and is rotated in an arrow L direction or an arrow R direction (see FIG. 1) by actuation of the rotary actuator 54. Note that as long as the head base 52 is rotatably configured, the drive source of the rotary actuator 54 may be a motor, such as, for example, a stepping motor or the like, or, for example, an air cylinder or the like.

In the measurement unit 50, a head unit 56 is provided to the head base 52. As shown in FIG. 1, the head unit 56 is provided with a single light source head 58 that serve as an illumination component of excitation light and plural light receiving heads 60 that serve as light receiving components. The light source head 58 and the light receiving heads 60 are attached to the head base 52. In the optical measurement device 14, there are 11 individual light receiving heads 60A, 60B, 60C, 60D, 60E, 60F, 60G, 60H, 60I, 60J, and 60K disposed in a shape radiating out from the axial center of the head base 52, at respective increments of 30° from the light source head 58, such that the sample holder 30 passes through between the light source head 58 and the light receiving heads 60.

The light source head 58 illuminates, as excitation light, light of a specific wavelength from a light emitting element, not shown in the figures, onto the sample holder 30. Further, the light receiving heads 60 are equipped with light receiving elements, not shown in the figures, and an fluorescent substance, internally administered to the mouse 12 accommodated in the sample holder 30, generates light due to the excitation light, and the light receiving heads 60 receive the fluorescent light emitted from the external peripheral portion of the sample holder 30, and output electrical signals according to the amount of light received (intensity of fluorescent light).

In the measurement unit 50, the light source head 58 and the light receiving heads 60 are disposed such that the emission point of the light source head 58 and the light reception points of the light receiving heads 60 all fall in the same flat plane. In the optical measurement device 14, this flat plane is orthogonal to the movement direction of the sample holder 30, and is the measurement plane, which is the flat plane through which the mouse 12 in the sample holder 30 passes. In the optical tomography measurement system 10, regeneration of optical tomographic images is performed along this measurement plane.

The measurement unit 50 illuminates excitation light emitted from the light source head 58 towards the sample holder 30 passing through the measurement plane, and receives the fluorescent light emitted from the periphery of the sample holder 30 with each of the light receiving heads 60. Further, in the measurement unit 50, the head base 52 is rotated, by a specific angle θ each time, by the rotary actuator 54 described above, and measurement of the fluorescent light is performed at each of the rotation positions. Note that in the present exemplary embodiment, measurement of the fluorescent light is performed in each of the positions as the light source head 58 is rotated by 30° (θ=30° each time, measurement of fluorescent light is performed at each of the positions, and measurements are performed 12 times for each single measurement plane.

As shown in FIG. 8, a rectangular shaped opening section 46A is formed in the separator 46, below the through hole 48. As shown in FIG. 7 and FIG. 8, a sliding base 62 is provided to the measurement unit 50. The sliding base 62 is formed in a belt shape, inserted through the opening section 46A of the separator 46 such that one end side of the sliding base 62, in the length direction, is on the measurement section 22 side of the opening section 46A, and the other end side thereof is on the loading section 20 side.

A slider 64 is disposed below the sliding base 62. The slider 64 is attached to the base plate 44 through brackets 66A and 66B. The slider 64 moves a support base 64A along the movement directions of the sample holder 30 (the arrow A direction and the opposite direction to the arrow A direction) using a feed screw mechanism, not shown in the figures.

The sliding base 62 is attached to the support base 64A. Consequently, the sliding base 62 moves in the arrow A direction, or the opposite direction to the arrow A direction, due to the slider 64 being moved by a motor, such as, for example, a stepping motor, not shown in the figures.

A leg 68 is provided projecting up from the sliding base 62 at the measurement section 22 side thereof, and a leg 70 is provided standing up from the sliding base 62 at the loading section 20 side thereof. A flat plate shaped arm 72 is provided to the leg 68, facing towards the loading section 20 side, and a leading end bracket 74 is attached to a leading end portion of the arm 72. A rear end bracket 76 is attached to the leg 70 so as to face the leading end bracket 74.

As shown in FIG. 6A, the leading end bracket 74 is formed in a substantially circular column shape, with a support lug 74A, to which the arm 72 is fixed, extending out at one axial direction end of the leading end bracket 74. Further, at the other axial direction end of the leading end bracket 74, a recess portion 78 is formed, for inserting the reference surface 36 side end of the sample holder 30 therein, and a bearing portion 80 is also formed. The sample holder 30 is supported by the leading end bracket 74 in a case in which the leading end portion of the sample holder 30 is in an inserted state into the recess portion 78 of the leading end bracket 74 and housed on the bearing portion 80.

Further, a substantially triangular shaped projection 80A is formed to the bearing portion 80 of the leading end bracket 74. As shown in FIG. 5, substantially triangular shaped recesses 34B (one is not shown in FIG. 5) are formed at a leading end portion and a rear end potion, respectively, of the lower mold block 34 of the sample holder 30.

In the leading end bracket 74 shown in FIG. 6A, the bottom face of the recess portion 78 configures a reference surface 78A, and the leading end bracket 74 is attached to the arm 72 such that the reference surface 78A is in a specific position. The sample holder 30 is positioned in the axial direction (movement direction) by the reference surface 36 contacting the reference surface 78A of the leading end bracket 74, and the sample holder 30 is positioned in the rotation direction (circumferential direction) by the projection 80A of the bearing portion 80 fitting into the recesses 34B. Note that through holes 74B are formed in the leading end bracket 74 facing the air holes 40 of the sample holder 30, and air can pass through to inside of the sample holder 30, where the mouse 12 is accommodated, in a case in which the sample holder 30 is in a state in which the reference surface 36 has contacted the reference surface 78A of the leading end bracket 74.

As shown in FIG. 6B, the rear end bracket 76 is formed in a substantially circular column shape, with one axial direction end of the rear end bracket 76, facing the sample holder 30, formed with a recess portion 82 and formed with a bearing portion 84. A substantially triangular shaped projection 84A is also formed to the bearing portion 84, facing the recesses 34B of the sample holder 30.

The sample holder 30 is supported by a rear end portion thereof fitting into the recess portion 82 of the rear end bracket 76 and being mounted on the bearing portion 84. At such a time, rotation of the sample holder 30 is prevented by the projection 84A of the bearing portion 84 being inserted into the recesses 34B formed in the lower mold block 34. The sample holder 30 is thereby positioned within the optical measurement device 14. Note that a groove shaped recess 76A is formed to the rear end bracket 76 along the axial direction thereof, and the tail of the mouse 12, protruding out from the sample holder 30, is accommodated in the recess 76A.

As shown in FIG. 6B and FIG. 6C, a base portion 86 of rectangular shaped cross-section is formed at the bottom face side of the rear end bracket 76. As shown in FIG. 6B, through holes 88 are formed to the base portion 86, passing through in a direction orthogonal to the axial direction of the rear end bracket 76. The through holes 88 are elongated holes with their length direction along the axial direction of the rear end bracket 76.

Figure 9:
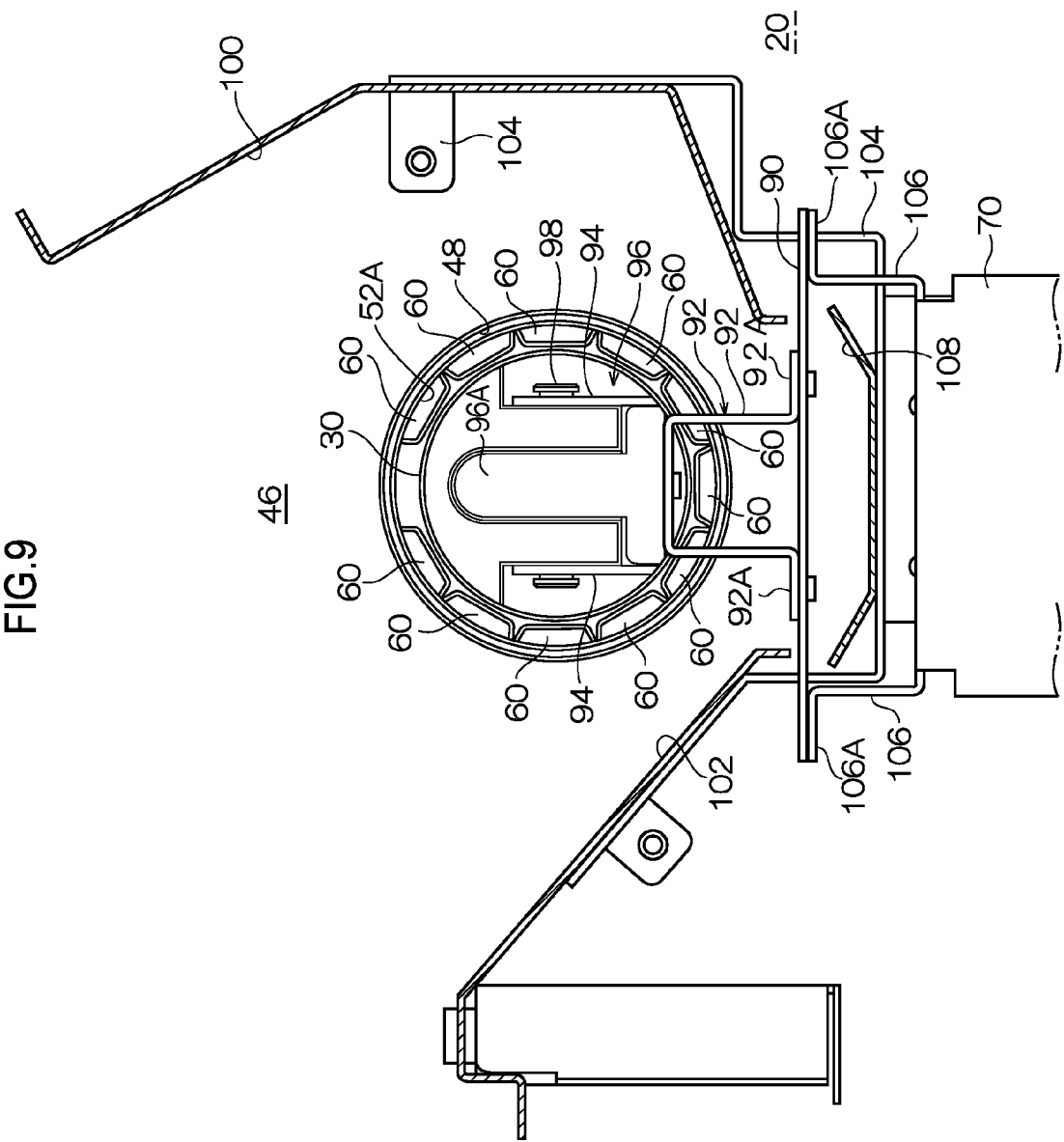
FIG. 9 is a schematic diagram showing the vicinity of a loading position of a sample holder in a loading section.

As shown in FIG. 8 and FIG. 9, a rectangular shaped plate member 90 is provided to the leg 70, with a seat 92 attached onto the top of the plate member 90. As shown in FIG. 6C, a pair of brackets 92A are formed to the seat 92, and the brackets 92A are attached and fixed to the plate member 90.

A bearing member 96 is provided to the seat 92, formed in a rail shape by a pair of standing walls 94 (one is not shown in FIG. 6C), and base portion 86 of the rear end bracket 76 is fitted in between the standing walls 94 of the bearing member 96. The rear end bracket 76 is attached to the bearing member 96 by pins 98 inserted through the through holes 88 (see FIG. 6B). At this time, the rear end bracket 76 is movable along the axial direction due to the through holes 88 being elongated. Further, a holding plate 96A is attached to the bearing member 96 facing an end portion of the rear end bracket 76, and a recess 76B is formed in the rear end bracket 76, into which the holding plate 96A is inserted.

The rear end bracket 76 is biased towards the leading end bracket 74 in the movement direction of the sample holder 30 (arrow A direction) by a biasing component, not shown in the figures, such as, for example, a coil spring, or the like, disposed in the recess 76B. Due thereto, the sample holder 30 mounted between the leading end bracket 74 and the rear end bracket 76 is retained biased towards the leading end bracket 74 by the rear end bracket 76. The sample holder 30 is detachable from between the leading end bracket 74 and the recess portion 78 by moving the rear end bracket 76 against biasing force from the biasing component.

As shown in FIG. 4, FIG. 8 and FIG. 9, a guide plate 100 is provided to the loading section 20 at the device far side, and a guide plate 102 is also provided thereto at the near side. As shown in FIG. 9, the guide plate 100 is folded around so as to form a protrusion out towards the device far side (the right hand side of the paper in FIG. 9), and the guide plate 102 is inclined from the device near side (the left hand side of the paper in FIG. 9) so as to be lower at the device far side.

As shown in FIG. 4, top edge portions of the guide plate 100 and the guide plate 102 reach to peripheral edge potions of the loading aperture 26, and due thereto, the sample holder 30 is retained between the guide plates 100 and 102, and between the leading end bracket 74 and the rear end bracket 76. Note that the guide plates 100 and 102 are fixed at the measurement section 22 side to the separator 46 by a bracket 104, and fixed at the opposite side to that of the measurement section 22 to a frame, not shown in the figures.

As shown in FIG. 8 and FIG. 9, a pair of standing walls 106 are provided at portions at the top ends of the leg 70, and the bottom face of the plate member 90 is fixed to bracket portions 106A at the top ends of the standing walls 106. A bottom plate 108 is provided between the pair of standing walls 106.

As shown in FIG. 4 and FIG. 8, the bottom plate 108 is formed in a belt plate shape, disposed such that its length direction is along the movement direction of the sample holder 30. As shown in FIG. 9, the bottom plate 108 is supported by the bracket 104, and both width direction edges of the bottom plate 108 extend out below the guide plates 100 and 102, respectively, and the bottom plate 108 bends such that the leading end portions thereof face upwards.

Namely, the bottom plate 108 extends out at the bottom side of the guide plate 100 and the guide plate 102, and the sample holder 30 loaded into the loading section 20 is surrounded by the guide plate 100, the bottom plate 108, and the guide plate 102.

Further, as shown in FIG. 8 and FIG. 9, each of the edge portions of the plate member 90 for supporting the rear end bracket 76 are inserted, respectively, between the guide plate 100 and the bottom plate 108, and between the guide plate 102 and the bottom plate 108. Further, as shown in FIG. 9, the pair of standing walls 106 on the leg 70 are disposed at the outside of the bottom plate 108 (the device near side and device far side of the bottom plate 108), with the plate member 90 and the bracket portions 106A connected below the guide plates 100 and 102.

Due thereto, the sample holder 30 is moved between the guide plates 100 and 102, and above the bottom plate 108 by moving the leg 70 below the bottom plate 108.

In the optical measurement device 14, by disposing the sample holder 30 within a space surrounded by the guide plate 100, the bottom plate 108, and the guide plate 102, if, for example, the mouse 12 within the sample holder 30 defecates, then even if this defecation flows out from the sample holder 30, since it is collected on the bottom plate 108, the inside of the device is not soiled, and internal cleaning of the device is facilitated.

As shown in FIG. 1, a control section 110 is provided to the optical measurement device 14, and measurement of fluorescent light is controlled by the control section 110. In a case in which measurement data has been acquired, the control section 110 outputs the acquired measurement data to the data processing device 16.

As shown in FIG. 2, the data processing device 16 is configured with a computer of general construction, equipped, for example, with a CPU 112, ROM 114, RAM 116, a HDD 118, serving as storage component, an input device 122, such as, for example, a keyboard 120 (see FIG. 1) and mouse, and a monitor 124, connected together by a bus 126.

An input-output interface (I/O IF) 128 is provided to the data processing device 16, and the input-output interface 128 is connected to an input-output interface 130 provided to the control section 110 of the optical measurement device 14. Note that connection between the optical measurement device 14 and the data processing device 16 not only can be made by a known standard, for example, RS-232 or the like, but also by application of any connection protocol.

In the data processing device 16 the CPU 112 controls operation of the optical measurement device 14 by executing a program stored in the ROM 114 or the HDD 118, using the RAM 116 as working memory, thereby measuring the intensity of fluorescent light generated from the mouse 12. Further, the data processing device 16 also reads in the measurement data obtained by measurement in the optical measurement device 14, and performs reconstruction of tomographic images representing the intensity distribution of fluorescent light, based on the measurement data.

A controller 132 equipped with a microcomputer is provided in the control section 110 of the optical measurement device 14, and this controller 132 is connected to the data processing device 16 via the input-output interface 130.

The control section 110 is equipped with: amps 136 that amplify electrical signals output respectively from a light generation drive circuit 134, for driving the light source head 58, and the light receiving heads 60; and an A/D converter 138 that, by performing A/D conversion on an electrical signal (analogue signal) output from the amp 136, generates a digital signal according to the analogue signal.

The control section 110 is also provided with a drive circuit 140 for driving a memory, not shown in the figures, of the rotary actuator 54, a drive circuit 142 for driving the motor, not shown in the figures, of the slider 64, and a display panel 144 for displaying the operation status of the optical measurement device 14, with the drive circuit 140, the drive circuit 142, and the display panel 144 connected to the controller 132. Note that, as shown in FIG. 3 and FIG. 4, the display panel 144 is provided, for example, at the device near side of the cover 24. The optical measurement device 14 is also, for example, preferably provided with a limit switch for detecting whether the sliding door 28 is open or closed, and provided with an interlock mechanism for maintaining the sample holder 30 in a stationary state in a case in which the sliding door 28 is in an open state.

Figure 10:
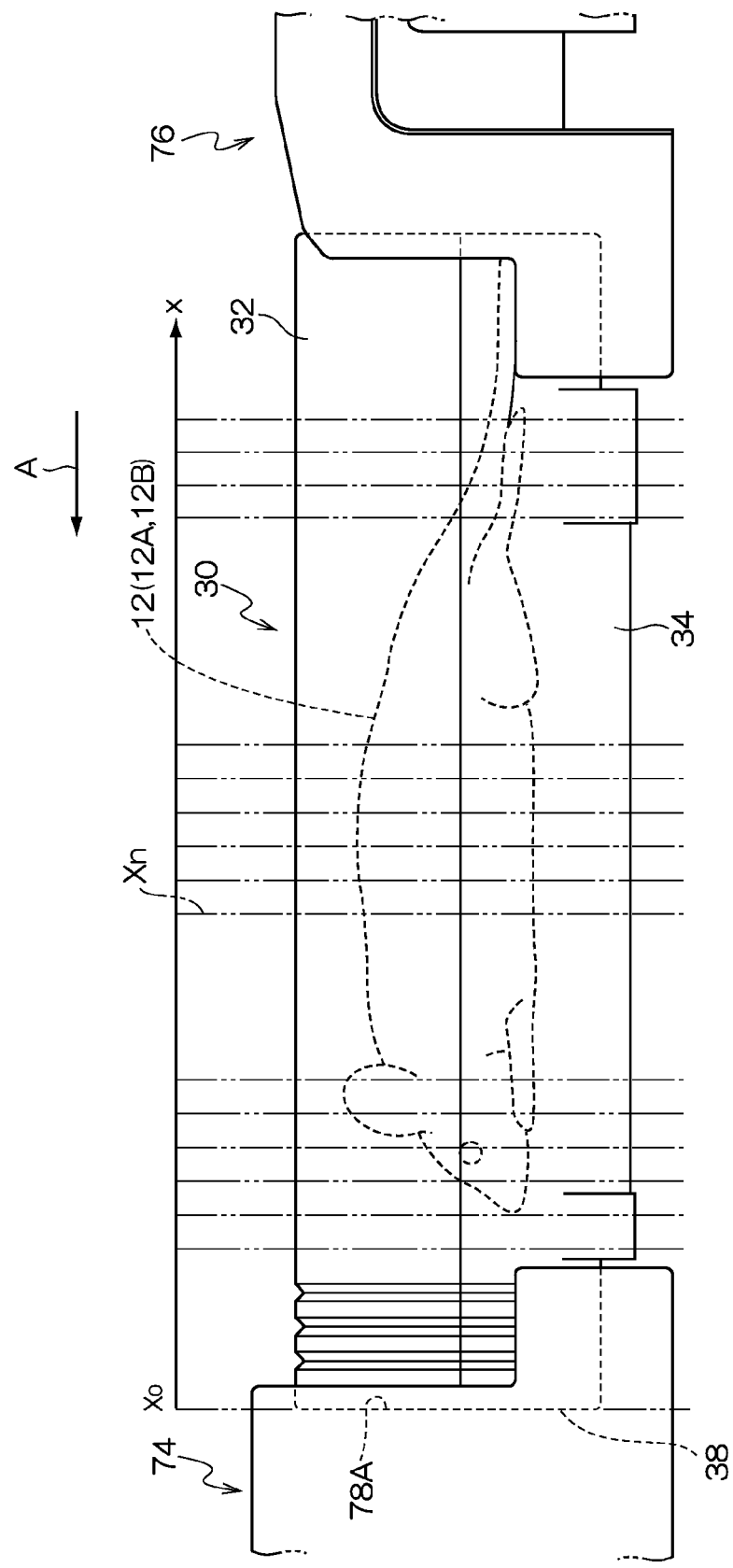
FIG. 10 is a schematic diagram showing measurement positions on a sample holder.

In the optical measurement device 14 provided to the optical tomography measurement system 10, the position of the reference surface 78A, which sets the sample holder 30 in the retaining leading end bracket 74, is ascertained in advance. The reference surface 36 of the sample holder 30 is made to contact the reference surface 78A. Then in the optical measurement device 14, as shown in FIG. 10, with the reference surface 36 as reference position $x_0$, measurement of the fluorescent light intensity is performed each specific interval, or at plural predetermined positions, as measurement positions x, moving the sample holder 30 to, and stopping it at, the respective measurement positions x.

At such times, the light source head 58 is rotated in the optical measurement device 14 by a specific angle θ each time from a predetermined origin position, and measurement of the fluorescent light intensity is performed at the origin position and each of the respective rotation positions using the 11 individual light receiving heads 60. Namely, with the position of the light source head 58 at angles $\theta_1$, $\theta_2$, to $\theta_{12}$, measurement data D (m) (where m identifies the respective light receiving head 60A to 60K), this being the output signals of the light receiving heads 60A to 60K, is read at respective angles θ. Measurement data D (x, θ, m) is thereby obtained. In a case of doing so, if the measurement positions x are the same, then the measurement data D (x, θ, m) are data in the same plane orthogonal to the movement direction of the sample holder 30.

Figure 11:
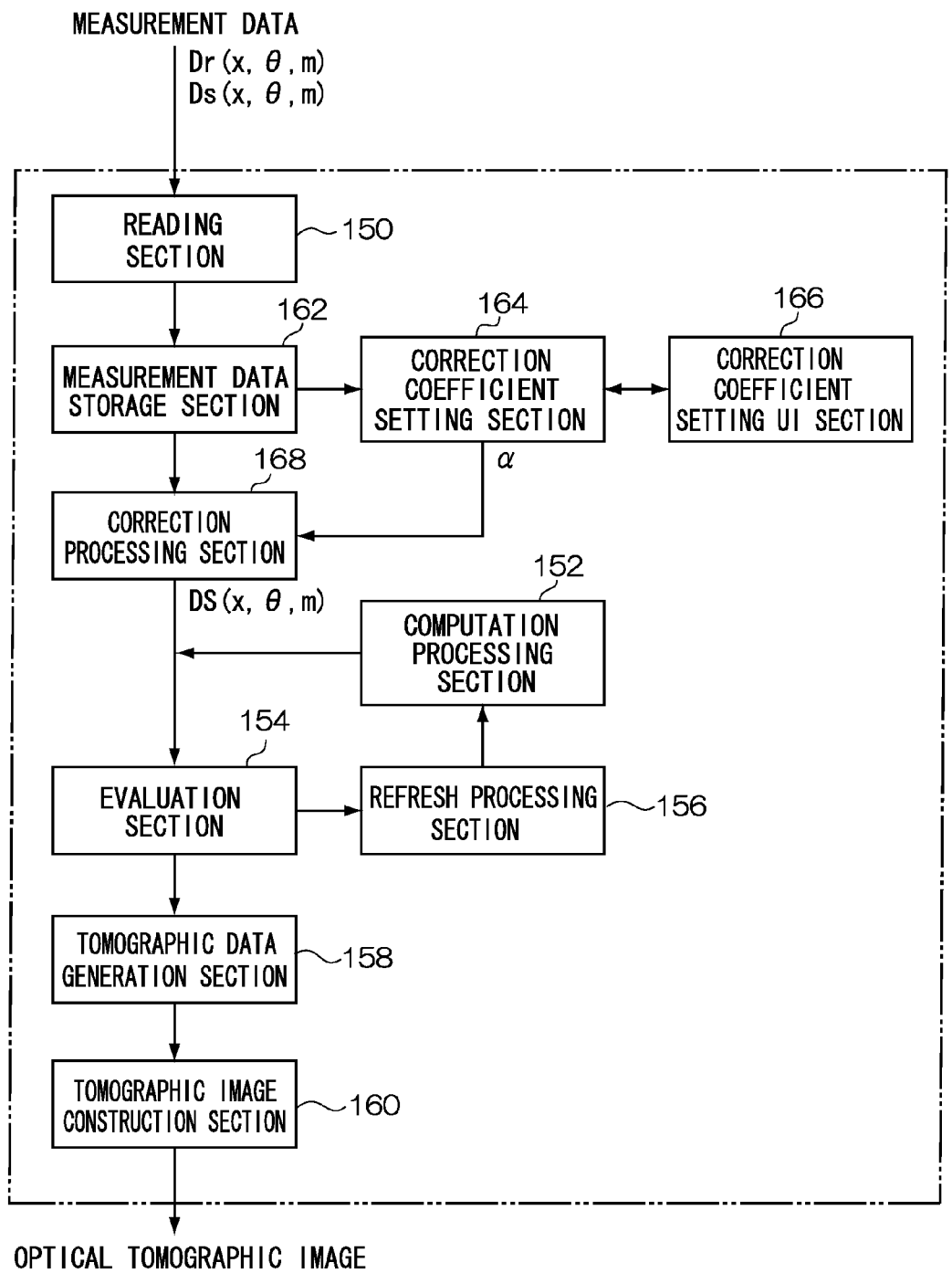
FIG. 11 is a functional block diagram of processing for measurement data in a data processing device.

As shown in FIG. 11, in the data processing device 16, a reading section 150, a computation processing section 152, an evaluation section 154, a refresh processing section 156, a tomographic data generation section 158 and a tomographic image construction section 160 are configured.

The reading section 150 reads in measurement data D (x, θ, m) measured by the optical measurement device 14. The computation processing section 152 computes the intensity of fluorescent light by forward computation employing a light diffusion equation, based on predetermined optical characteristic values including an absorption coefficient to light from a fluorescent substance internally administered to the mouse 12.

In the evaluation section 154, a difference between the computed fluorescent light intensity and the fluorescent light intensity obtained from the measurement data is evaluated. In the refresh processing section 156, by performing backwards computation using the light diffusion equation, the absorption coefficient is set so as to reduce the difference obtained from the evaluation section 154, based on the density distribution of the fluorescent bodies from the fluorescent light intensity. In addition, in a case in which the absorption coefficient is refreshed in the refresh processing section 156 based on the density distribution of the fluorescent substance, the computation processing section 152 computes the fluorescent light intensity using the refreshed absorption coefficient based on the density distribution of fluorescent substance.

In this manner, by repeatedly refreshing and evaluating the fluorescent light intensity, for example, in a case in which the computed fluorescent light intensity is evaluated as matching the measurement data, a density distribution of fluorescent substance is generated in the tomographic data generation section 158, this being optical tomographic data from the absorption coefficient based on the density distribution of the fluorescent bodies in a case in which the values are evaluated as matching, and an optical tomographic image based on this optical tomographic data is generated in the tomographic image construction section 160.

In such a manner, after the data processing device 16 has performed specific data processing on the measurement data D (x, θ, m) read in from the optical measurement device 14, an optical tomographic image of the mouse 12 is reconstructed based on the measurement data D (x, θ, m) by performing image processing based on the processing results.

Note that the reconstruction of the optical tomographic image can appropriately apply any configuration that is a configuration from measuring the fluorescent light intensity of the fluorescent substance, and using computation results from a light transport equation and/or from a light diffusion equation based on the measurement data D (x, θ, m) obtained from the measuring.

In the optical tomography measurement system 10, in a case of forming the optical tomographic image of the mouse 12, before making measurements of the mouse 12 that is the measurement subject (referred to below as sample mouse 12A), measurement data for standardization correction is acquired (referred to below as measurement data Dr (x, θ, m)). Based on the measurement data Dr (x, θ, m) and measurement data of the sample mouse 12A (referred to below as measurement data Ds (x, θ, m)), corrected measurement data DS (x, θ, m) is generated in which the measurement data Ds (x, θ, m) of the sample mouse 12A has been corrected. In the optical tomography measurement system 10, reconstruction of optical tomographic images is performed using the corrected measurement data DS (x, θ, m).

As shown in FIG. 11, in the data processing device 16 a measurement data storage section 162, a correction coefficient setting section 164, a correction coefficient setting UI section 166, and a correction processing section 168 are configured.

The measurement data Dr (x, θ, m) employed for correction read from the optical measurement device 14, and the measurement data Ds (x, θ, m) of the sample mouse 12A are stored in the measurement data storage section 162. A correction coefficient α is set in the correction coefficient setting section 164, for correcting the measurement data Ds (x, θ, m), based on the measurement data Dr (x, θ, m) and the measurement data Ds (x, θ, m).

in a case of setting this correction coefficient α, the correction coefficient setting UI section 166, configuring a selection component, displays on a specific user interface (UI), for example on the monitor 124, flat planes including a site of interest for in a case of setting the correction coefficient α, for selecting, as a region of interest, a measurement position x on the mouse 12 corresponding to the region of interest (referred to below as measurement position xn). Also in the correction coefficient setting UI section 166, the angle θ of the light source head 58 is set at the selected measurement position xn and the data D(m) of which of the light receiving heads 60A to 60K to be employed is set.

The correction coefficient setting section 164 sets the correction coefficient α such that the measurement data Ds (m) is cancelled out by the measurement data Dr (m), with the data Dr (m), from one or other of the measurement data Dr (xn, θ, m) at the measurement position xn set as the region of interest, as second measurement data, and with the measurement data Ds (m) in the measurement data Ds (xn, θ, m) (measurement data with the same angle θ of the light source head 58, output from the same light receiving head 60) as second correction measurement data. Namely, the correction coefficient α is set such that Dr(m)−α·Ds(m)=0.

The correction processing section 168 corrects the measurement data Ds (x, θ, m) based on the correction coefficient α set by the correction coefficient setting section 164, and generates the corrected measurement data DS (x, θ, m) for measurement data to be employed in image reconstruction. In a case in which this is performed, for example, the correction processing section 168 computes:

$$DS(x,\theta,m)=Dr(x,\theta,m)-\alpha \cdot Ds(x,\theta,m).$$

Reconstruction of optical tomographic images is performed in the data processing device 16 using the corrected measurement data DS (x, θ, m) correction processed in the correction processing section 168.

Explanation follows of an example of correction of measurement data. A lesion site, such as, for example, a tumor or the like, is induced (generated) in advance in the mouse 12 that is the measurement subject in the optical tomography measurement system 10 (the sample mouse 12A) by, for example, injecting with diseased cells, such as, for example, tumor cells. Inducing the lesion site can be achieved by appropriate application of any known method.

In the optical tomography measurement system 10, an antibody is employed that specifically attaches to the lesion site formed in the sample mouse 12A, and by bonding a fluorescent substance to this antibody to give a fluorescent marking agent, the antibody bonded with the fluorescent substance (the fluorescent marking agent) is administered to the sample mouse 12A. Since known antibodies and known fluorescent substances can be appropriately employed here, illustration thereof is omitted.

In the sample mouse 12A administered with the fluorescent marking agent, the fluorescent marking agent disperses within the body due to the blood circulation system and the like, and the fluorescent marking agent at the periphery of the lesion site is attached to the lesion site by an antigen-antibody reaction. The fluorescent substance is thereby specifically attached to the lesion site in the sample mouse 12A. By illuminating excitation light onto the sample mouse 12A in this state, the fluorescent substance attached to the lesion site in the body of the sample mouse 12A generates fluorescent light.

In the optical tomography measurement system 10, the sample mouse 12A administered with the fluorescent marking agent is accommodated in the sample holder 30, loaded into the optical measurement device 14 at a specific timing, and measurement of the intensity of fluorescent light generated from the fluorescent substance is performed (acquiring the measurement data Dr (x, θ, m)). For the timing of performing measurement of the sample mouse 12A in the optical measurement device 14, the duration that passes from administering the fluorescent marking agent to the sample mouse 12A until the fluorescent substance attaches to the lesion site is estimated, and measurement is performed at this timing.

However, there are occasions in a case in which more than a little unwanted light caused by the device, or unwanted light caused measurement subject, is incident to the light receiving heads 60A to 60K. Unwanted light caused by the device is sometimes:

a cogenerated light generated from a semiconductor laser used as a light generation element in the light source head 58;

b leakage of excitation light emitted from the light source head 58, occurring due to the properties of an excitation light color filter; or c electrical noise.

Unwanted light caused by the measurement subject is sometimes:

e fluorescent light generated by the measurement subject itself;

f fluorescent light generated by the fluorescent substance, or by the antibody bonded to the fluorescent substance, accumulated or dispersed at non-specific sites; or g scattered light and fluorescent light due, for example, to the contents of the digestive tract of the measurement subject.

In a case in which such unwanted light is received as light by the light receiving heads 60 and included in the measurement data, not only is it difficult to reconstruct an appropriate optical tomographic image, but sometimes reconstruction itself of an optical tomographic image even becomes impossible. Note that unwanted light caused by the contents of the digestive tract of the measurement subject may be removed by adjusting the food given, or by forcible elimination using, for example, a medicine or the like.

In the optical tomography measurement system 10, before measuring the sample mouse 12A, the measurement data Dr (x, θ, m) for use in correction is generated. A mouse (referred to below as control mouse 12B) having an equivalent frame (equivalent body shape) to that of the sample mouse 12A is employed in generation of the measurement data Dr (x, θ, m) for use in correction. The mouse 12 employed as the control mouse 12B is a mouse 12 having the same body frame (body length, weight, and the like) as the mouse 12 employed as the sample mouse 12A, such that the age in months (years) representing the number of weeks passed since birth is substantially the same. Namely, mice 12 having substantially the same positions of internal organs and body parts are employed for the sample mouse 12A and the control mouse 12B.

In the present exemplary embodiment, the difference between the sample mouse 12A and the control mouse 12B is that, whereas a lesion site is induced in the sample mouse 12A, diseased tissue is not injected into the control mouse 12B, and a lesion site is not induced. Furthermore, in contrast to being administered with a fluorescent marking agent, the control mouse 12B is not administered with an antibody including a fluorescent substance (fluorescent marking agent or the like).

Figure 12:
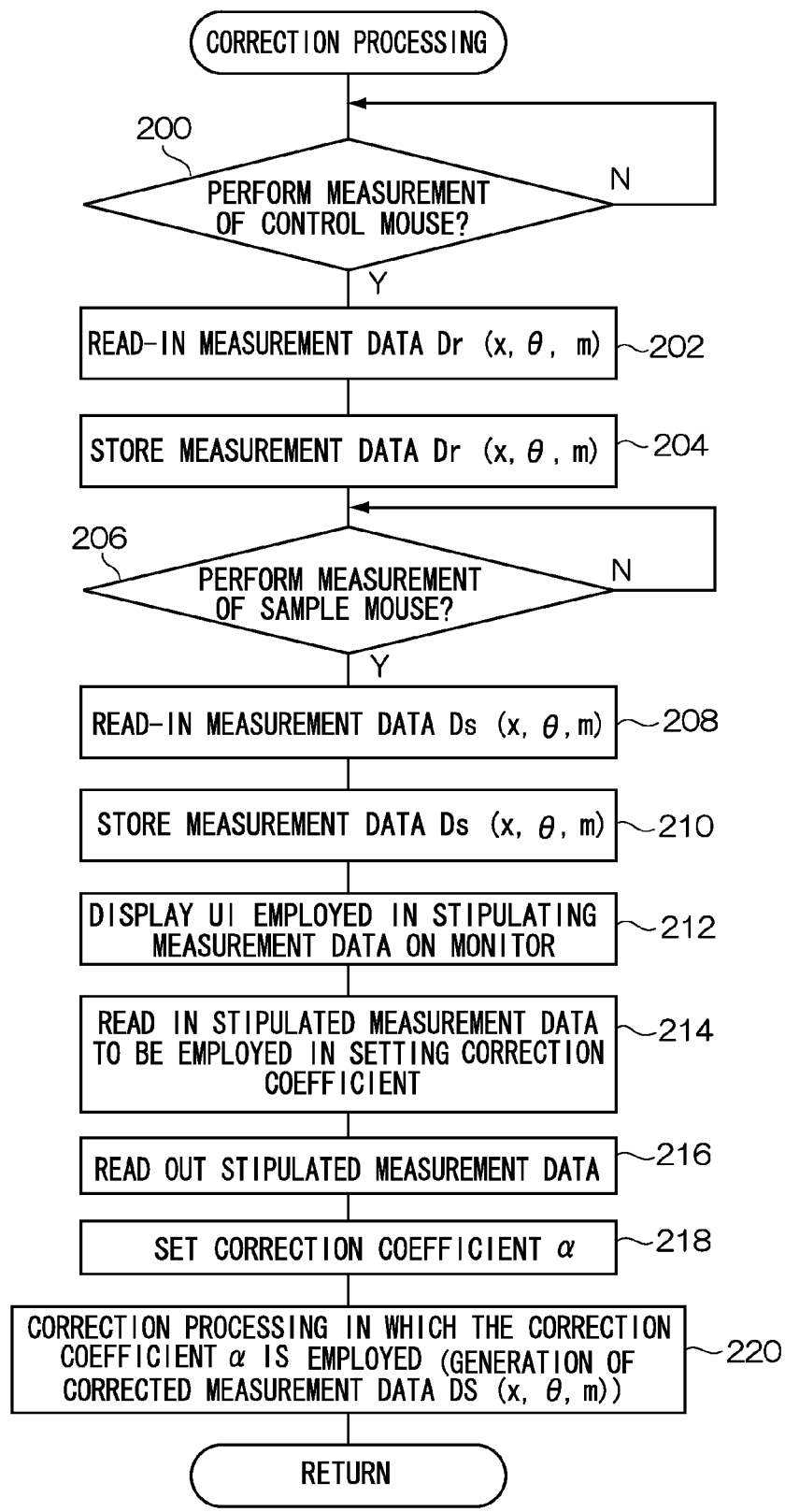
FIG. 12 is a flow diagram showing an example of measurement data correction processing.

FIG. 12 shows an outline of measurement processing (correction processing) according to the present exemplary embodiment. In a case of performing correction processing, the measurement data Dr (x, θ, m) is acquired as well as the measurement data Ds (x, θ, m). In the flow chart, at the first step 200, confirmation is made as to whether or not measurement is to be performed to the control mouse 12B, and in a case in which commencement of measurement to the control mouse 12B is instructed, affirmative determination is made at step 200, and processing proceeds to step 202. At step 202, the measurement data Dr (x, θ, m) output from the optical measurement device 14 is read in, and the read-in measurement data Dr (x, θ, m) is stored in the measurement data storage section 162 (step 204).

Next, at step 206, confirmation is made as to whether or not measurement is to be performed to the sample mouse 12A. In a case in which measurement is to be made to the sample mouse 12A, this is performed after a specific set duration has elapsed since administration of the fluorescent marker agent. Note that this duration may be determined, for example, from the type, body frame, and the like of the mouse 12, and can be calculated in advance.

In a case in which commencement of measurement of the sample mouse 12A is instructed, affirmative determination is made at step 206, and the processing proceeds to step 208. At step 208, the measurement data Ds (x, θ, m) output from the optical measurement device 14 is read in, and the read-in measurement data Ds (x, θ, m) is stored in the measurement data storage section 162 (step 210).

In a case in which the measurement data Dr (x, θ, m) of the control mouse 12B and the measurement data Ds (x, θ, m) of the sample mouse 12A have been acquired, at the next step 212, the measurement data D(m) to be utilized in setting the correction coefficient α is stipulated.

Stipulation of the measurement data D(m), at step 212, employs a specific UI, for example, as shown in FIG. 10, displaying a model of the mouse 12 and the sample holder 30 on the monitor 124, for stipulation by selecting on the display the measurement position xn as the region of interest on the mouse 12, using the input device 122.

In a case in which this measurement position xn is stipulated, a measurement position x is selected that does not include the lesion site (a position where fluorescent substance is not attached), such as, for example, the measurement position xs of FIG. 10. In a case of doing so, the measurement position xn for selection is preferably one that is near to the lesion site.

In a case in which the measurement position xn has been stipulated, next, the measurement data Dr (xn, θ, m) and the measurement data Ds (xn, θ, m) corresponding to the measurement position xn are displayed on the monitor 124.

Figure 13A:
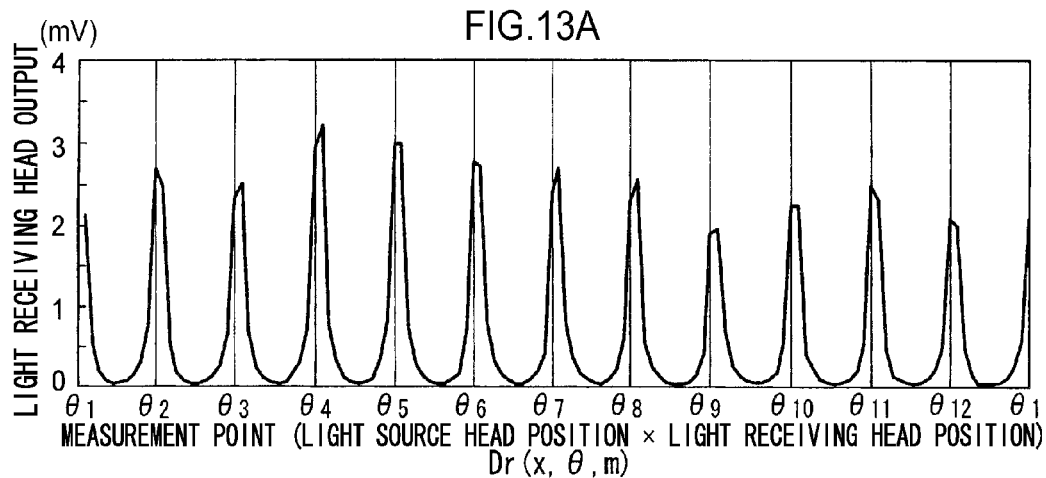
FIG. 13A is a graph showing measurement data $Dr(x, \theta, m)$ used for setting a correction coefficient.
Figure 13B:
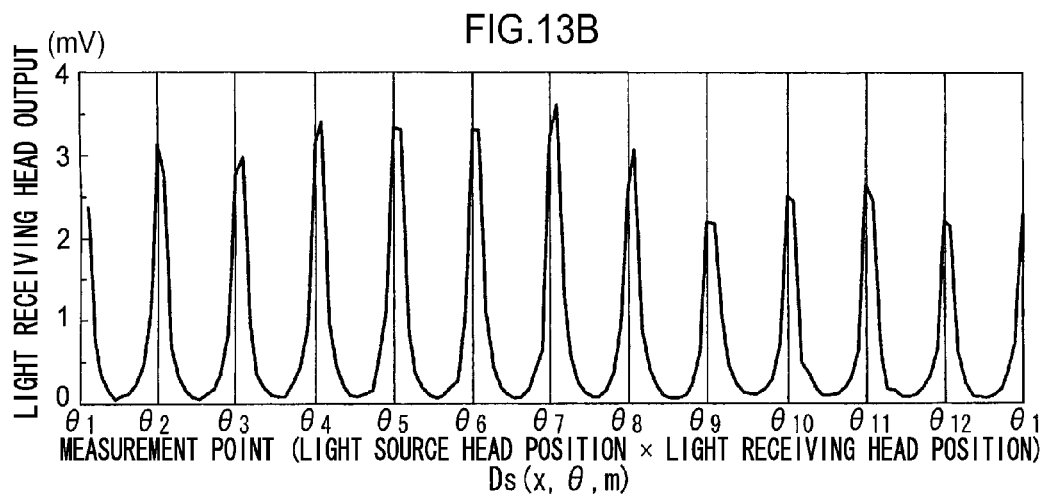
FIG. 13B is a graph showing measurement data $Ds(x, \theta, m)$ used for setting a correction coefficient.
Figure 13C:
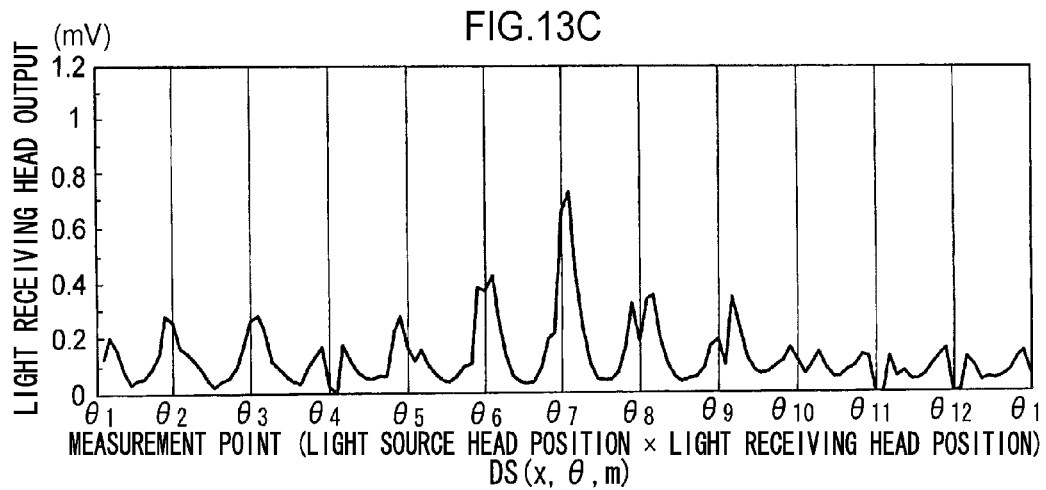
FIG. 13C is a graph showing corrected measurement data $DS(x, \theta, m)$ generated based on a correction coefficient.

FIG. 13A and FIG. 13B show examples thereof. Note that in FIG. 13A, the measurement data Dr (xn, θ, m) obtained from the control mouse 12B is displayed, and in FIG. 13B the measurement data Ds (xn, θ, m) obtained from the sample mouse 12A is displayed. In FIG. 13A to FIG. 13C, and in FIG. 14A to FIG. 14C, the positions of the light source head 58 are shown by $\theta_1$ to $\theta_{12}$, and the outputs of the light receiving heads 60A to 60K at this time (measurement value: measurement data D(m), are displayed in sequence). Namely, the outputs of the light receiving heads 60A to 60K in a case in which the light source head 58 is positioned at angle $\theta_1$ are shown between the angle $\theta_1$ and $\theta_2$, in sequence starting from the output of the light receiving head 60A.

In a case of selecting here the measurement data D(m) for setting the correction coefficient α, the measurement data Dr (xn, θ, m) employed for correction is preferably the maximum value. In FIG. 13A, preferably selection is made of the output values of the light receiving head 60A in a case in which the light source head 58 is positioned at $\theta_4$ (denoted below as measurement data Dr(m) and measurement data Ds(m)).

As described below, since the correction coefficient α is for the ratio of the measurement data Dr(m) relative to the measurement data Ds(m), if the output value is small, in a case in which correction is performed using a correction coefficient α derived from such an output value, then sometimes large errors occur. Therefore, one or other either the greatest value in the set measurement position xn, or a value that is greater than a preset reference value therein, is preferably selected.

Note that there is no limitation thereto, and the output of any of the light receiving heads 60 in a case in which the light source head 58 is in any of the positions can be appropriately applied. Further, in the present exemplary embodiment, a model of the sample holder 30 and the mouse 12 is displayed on the monitor 124, and the measurement data Dr(m), Ds(m) are selected from the measurement data Dr (x, θ, m) and Ds (x, θ, m), however there is no limitation thereto. For example, various configurations may be appropriately applied in which a preset measurement position x and output of a preset light receiving head 60 are employed.

By employing mice of equivalent body frames for the sample mouse 12A and the control mouse 12B, equivalent sites in the sample mouse 12A and the control mouse 12B, respectively, can be used for the measurement data Dr(m), Ds(m).

In a case in which the measurement data is stipulated in this manner, in the flow chart in FIG. 12, the stipulated measurement data (stipulated measurement position xn and light receiving head 60) is read in at step 214, and the processing then proceeds to step 216. In step 216, the corresponding measurement data Dr(m) and Ds(m) are read in from the measurement data Dr (x, θ, m) and the measurement data Ds (x, θ, m). Here, in a case in which the output of the light receiving head 60A at angle $θ_4$ has been stipulated, the corresponding measurement data (output values) are read out as the measurement data D(m), Ds(m) from the measurement data Dr (xn, θ, m) and the measurement data Ds (xn, θ, m).

At the next step 218, the read-in measurement values (measurement data Dr(m), Ds(m)) are used to set the correction coefficient α. For example, if the measurement data (output value) Dr (m) in the measurement data Dr (xn, θ, m) is 3.222 (mV), and the measurement data (output value) Ds (m) in the measurement data Ds (xn, θ, m) is 3.409 (mV), then the correction coefficient α obtained is:

$$α=Ds(m)/Dr(m)=3.409/3.222=1.058$$

In a case in which the correction coefficient α has been set in this manner, at step 220, correction processing is performed on the measurement data Ds (x, θ, m) using this correction coefficient α, computing the corrected measurement data DS (x, θ, m).

The correction processing here is performed on all of the data of the measurement data Ds (x, θ, m), and the corrected measurement data DS (x, θ, m) is compute as:

$$DS(x,θ,m)=Dr(x,θ,m)-α·Ds(x,θ,m).$$

FIG. 13C shows the corrected measurement data DS (xn, θ, m) at the stipulated measurement position xn in a case in which the correction coefficient α is set.

The corrected measurement data DS (x, θ, m), including the corrected measurement data DS (xn, θ, m), is preferably such that $DS(x, θ, m) \geq 0$, however data of negative values may be included therein.

Note that since output of the light receiving head 60 is never negative, in a case in which negative values are included in the corrected measurement data DS (x, θ, m), a new region of interest (measurement position xn) may be set from the measurement data Dr (x, θ, m) and the measurement data Ds (x, θ, m), a new correction coefficient α derived, and corrected measurement data DS (x, θ, m) computed using this correction coefficient α. In a case in which, even in this case, negative values (data) are included in the corrected measurement data DS (x, θ, m), the negative data may be replaced by "0", so as to arrive at $DS (x, θ, m) \geq 0$.

There is no limitation thereto, and in a case in which negative values are included in the corrected measurement data DS (x, θ, m) this data may be set at zero.

In this manner, in a case in which the corrected measurement data DS (x, θ, m) has been generated from the measurement data Dr (x, θ, m) of the control mouse 12B and the measurement data Ds (x, θ, m) of the sample mouse 12A, reconstruction of optical tomographic images using the fluorescent light is performed using this corrected measurement data DS (x, θ, m).

Figure 15A:
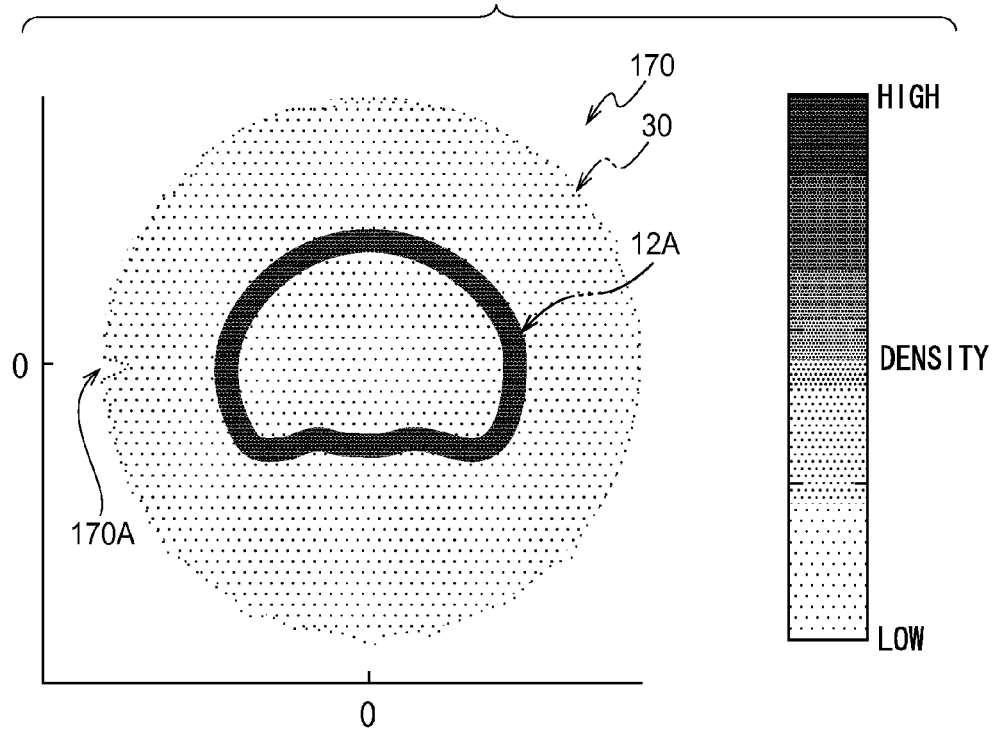
FIG. 15A is a schematic diagram showing an example of an optical tomographic image, and shows an optical tomographic image based on the measurement data of FIG. 13B.
Figure 15B:
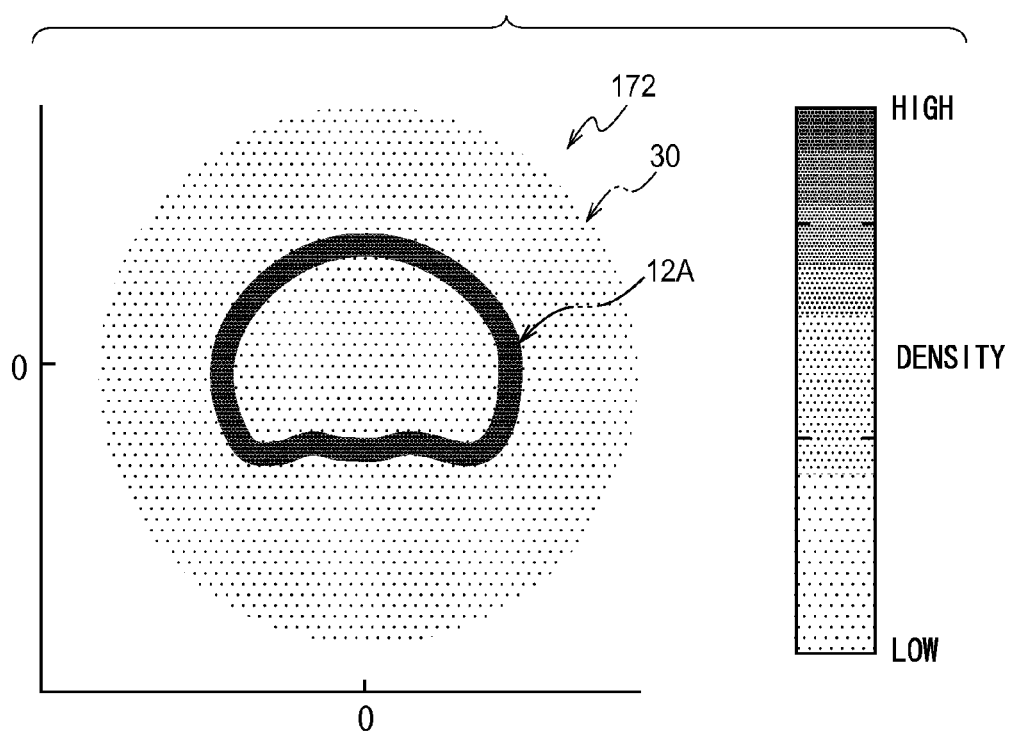
FIG. 15B is a schematic diagram showing an example of an optical tomographic image, and shows an optical tomographic image based on the corrected measurement data of FIG. 13C.

FIG. 15A shows, at the measurement position xn at which the correction coefficient α was set, an outline of an optical tomographic image 170 reconstructed using the uncorrected measurement data Ds (xn, θ, m), and FIG. 15B shows an outline of an optical tomographic image 172 reconstructed using the corrected measurement data DS (xn, θ, m) based on the correction coefficient α. Note that the optical tomographic images 170 and 172 represent, for example, the density according to the fluorescent light intensity. Further, in the optical tomographic images 170 and 172, density differences occur between the inside of the sample holder 30 and the peripheral edges of the sample holder 30, and between the mouse 12 (sample mouse 12A) in the sample holder 30 and the peripheral edges of the sample mouse 12A. The sample holder 30 and the sample mouse 12A inside the sample holder 30 are identifiable by these density differences.

As shown in FIG. 15A and FIG. 15B, there is no material amount of fluorescent substance present at the measurement position xn of the sample mouse 12A. Therefore, differences in the internal images are small between the optical tomographic image 170 reconstructed using the measurement data Ds (xn, θ, m) shown in FIG. 15A, and the optical tomographic image 172 reconstructed using the corrected measurement data DS (xn, θ, m) shown in FIG. 15B.

However, as shown in FIG. 15A, due to unwanted light components being contain in the measurement data Ds (xn, θ, m), artifacts are generated in the optical tomographic image 170 reconstructed using the measurement data Ds (xn, θ, m). Due thereto, a distortion (artifact 170A) occurs in the optical tomographic image 170 at a location corresponding the peripheral edge portion of the sample holder 30.

In contrast thereto, as shown in FIG. 15B, artifacts at positions corresponding to the peripheral edge portion of the sample holder 30 are suppressed in the optical tomographic image 172 reconstructed using the corrected measurement data DS (xn, θ, m), such that artifacts do not appear.

With the lesion site of the sample mouse 12A as an observation region, reconstruction of an optical tomographic image of the observation region is performed in the optical tomography measurement system 10. At this time, first measurement data of the measurement data Ds (x, θ, m) corresponding to the measurement position x including the observation region is taken as the first measurement data, and the measurement data Dr (x, θ, m) corresponding to the measurement position x is taken as first correction measurement data.

Figure 14A:
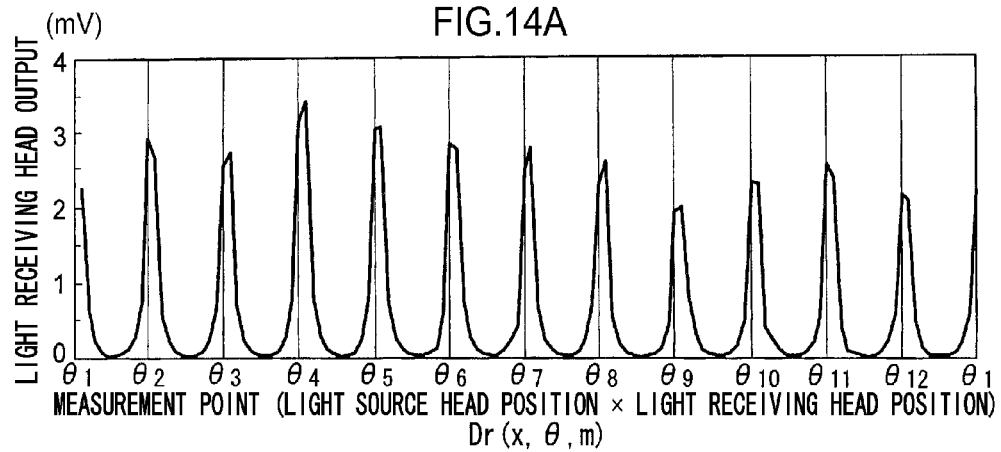
FIG. 14A is a graph showing measurement data $Dr(x, \theta, m)$ of a specific site.
Figure 14B:
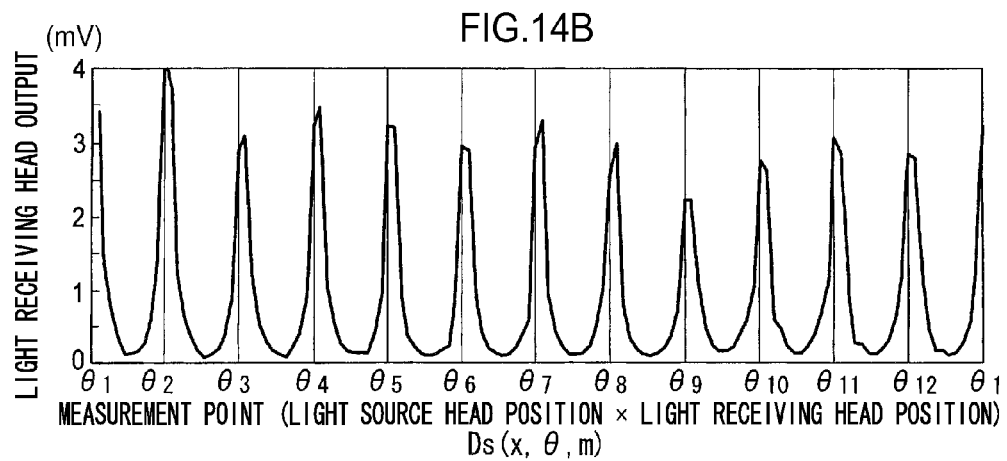
FIG. 14B is a graph showing measurement data $Ds(x, \theta, m)$ of a specific site.
Figure 14C:
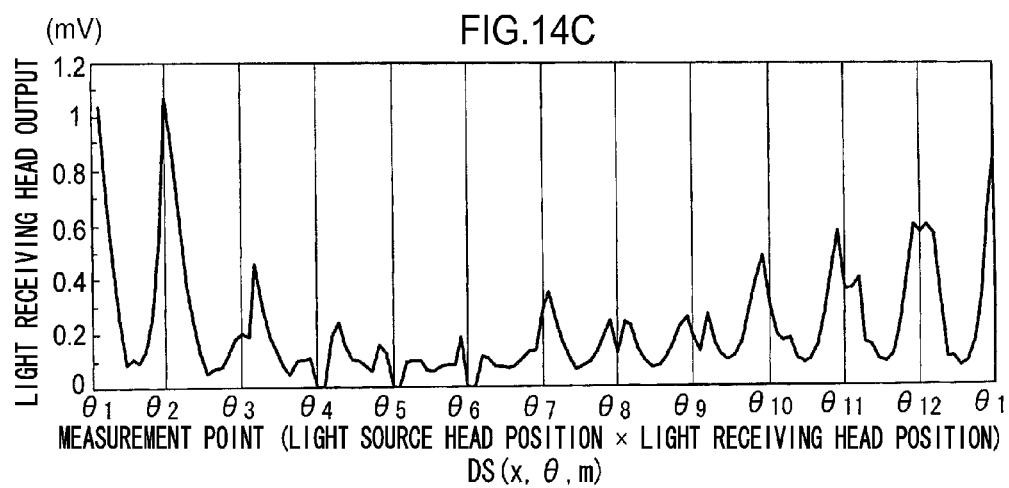
FIG. 14C is a graph showing corrected measurement data $DS(x, \theta, m)$ based on a correction coefficient generated from the measurement data of FIG. 14A and FIG. 14B.

FIG. 14B shows measurement data Ds (x, θ, m) of the sample mouse 12A corresponding to the measurement position x including the lesion site, and FIG. 14A shows measurement data Dr (x, θ, m) of the control mouse 12B at the same site. FIG. 14C shows corrected measurement data DS (x, θ, m) obtained using the correction coefficient α.

As shown in FIG. 14A and FIG. 14B, whereas it can be seen that a difference occurs between the output values (measurement data) of the light receiving head 60 between the measurement data Dr (x, θ, m) and the measurement data Ds (x, θ, m), they are, however, closely approximating output values. In contrast, the corrected measurement data DS (x, θ, m) shown in FIG. 14C not only looks different from the measurement data Dr (x, θ, m), but also looks different from the measurement data Ds (x, θ, m).

Namely, due to the measurement conditions in the optical measurement device 14 being the same between the sample mouse 12A and the control mouse 12B, an unwanted light component caused by the device is included in both the measurement data Dr (x, θ, m) and the measurement data Ds (x, θ, m). However, by setting the correction coefficient α such that the difference between the measurement data Dr (m) and the measurement data Ds (m) is zero, and by using this correction coefficient α, corrected measurement data DS (x, θ, m) can be generated in which the unwanted light component caused by the device (background noise) has been cancelled out.

Further, while the fluorescent substance is contained in the sample mouse 12A, the fluorescent substance is not contained in the control mouse 12B. Therefore, an unwanted light component in caused by the living organism (the mouse 12) itself can be cancelled out by using the correction coefficient α.

Figure 16A:
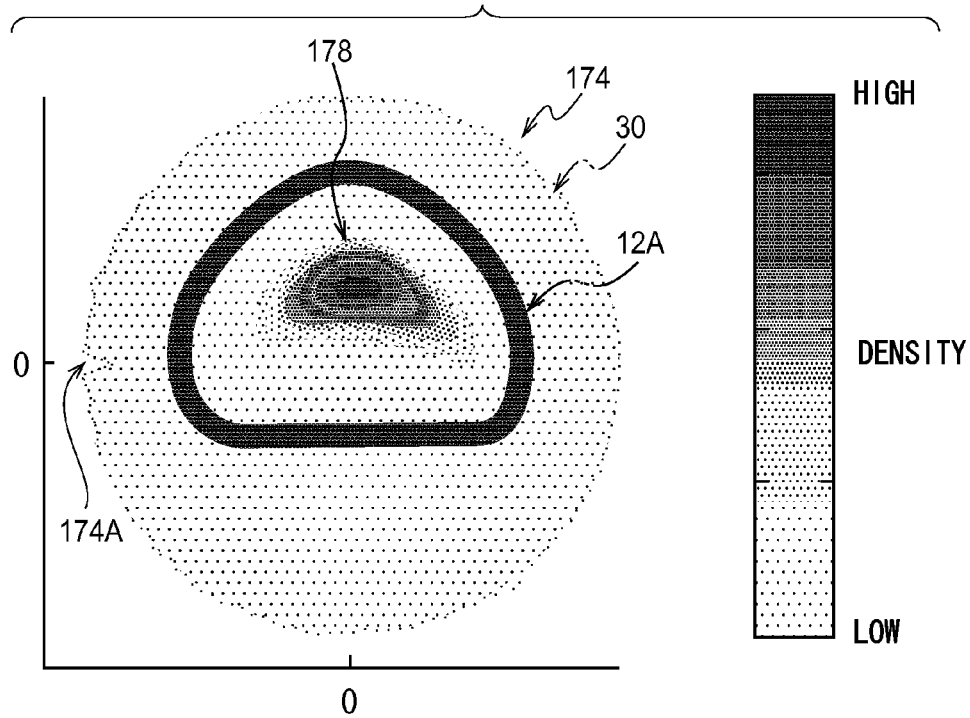
FIG. 16A is a schematic diagram showing an example of an optical tomographic image, and is an optical tomographic image based on the measurement data of FIG. 14B.
Figure 16B:
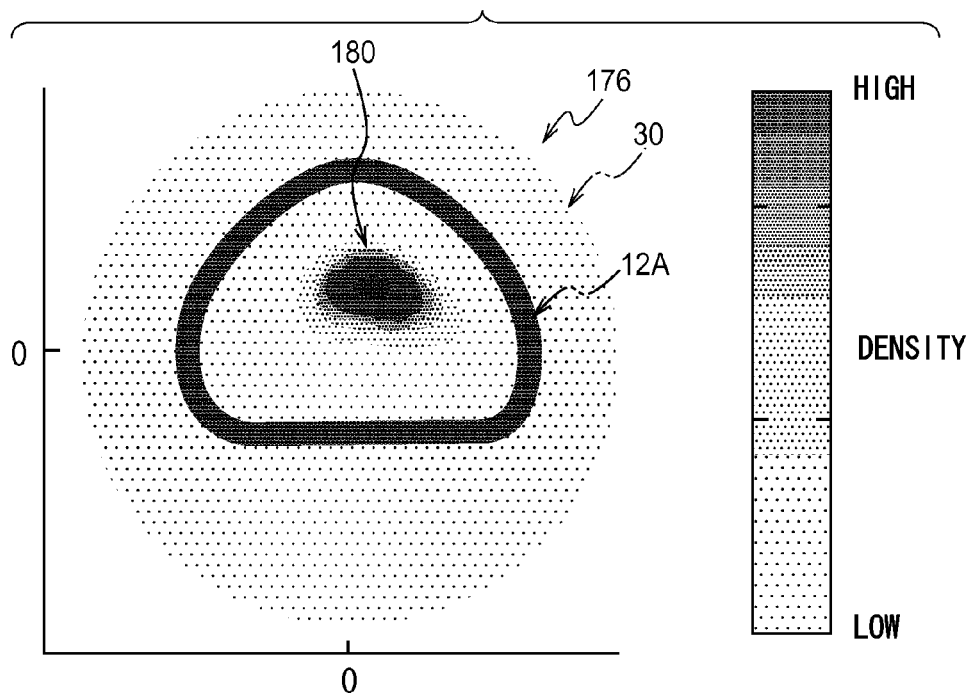
FIG. 16B is a schematic diagram showing an example of an optical tomographic image, and shows an optical tomographic image based on the corrected measurement data of FIG. 14C.

FIG. 16A shows an outline of an optical tomographic image 174 reconstructed based on the measurement data Ds (x, θ, m) of FIG. 14B, and FIG. 16B shows an outline of an optical tomographic image 176 reconstructed based on the corrected measurement data DS (x, θ, m) of FIG. 14C.

As shown in FIG. 16A, an artifact 174A is generated in the optical tomographic image 174 where the outer peripheral portion is indented towards the inside.

Further, in the sample mouse 12A, by the lesion site being included, the fluorescent substance is attached at this lesion site. Consequently, as the fluorescent light intensity gets higher at the lesion site, the lesion site is identifiable from an increased in the image density.

Generally, in optical tomographic images reconstructed using the measurement data Ds (x, θ, m) (see FIG. 16A), the fluorescent light intensity of the peripheral edge portion of the lesion site falls away, and the relative fluorescent light density of the lesion site also becomes lower.

Due thereto, as shown in FIG. 16A, in the optical tomographic image 174 reconstructed using the measurement data Ds (x, θ, m), resolution of the lesion site decreases at the outer peripheral portion, and the shape of a lesion site (site where the fluorescent substance is attached) image 178 becomes unclear.

In contrast, as shown in FIG. 16B, in the optical tomographic image 176 reconstructed using the corrected measurement data DS (x, θ, m), the lesion site, namely, an image 180 of the site where the fluorescent substance is attached, is clear.

Due thereto, by acquiring measurement data Dr (x, θ, m) for use in correction, using the control mouse 12B having no lesion site present and not administered with the fluorescent substance, and by correction of the measurement data Ds (x, θ, m) of the sample mouse 12A using this measurement data Dr (x, θ, m), the unwanted light components making up background noise can be removed from the measurement data Ds (x, θ, m). Due thereto, in the optical tomography measurement system 10, reconstruction of a high quality optical tomographic image is enabled for the sample mouse 12A.

The fluorescent substance, bonded to the antibody that specifically attaches to a specific site, is administered internally to the mouse 12, circulates internally and disperses due, for example, to blood flow and the like, the fluorescent substance also attaches to the specific region due to the antibodies at the peripheral region of the specific region attaching to the specific region, leading to the fluorescent light density of the specific region being raised. In contrast thereto, in a case in which fluorescent substance not bonded to an antibody that specifically attaches to the specific site (referred to below simply as fluorescent substance) is internally administered to the mouse 12, while it circulates and disperses internally due, for example, to blood flow and the like, since the fluorescent substance at the peripheral region of the specific site does not attach to the specific site, the fluorescent light density of the specific site remains in a low state.

In consideration of the above, for mice 12 having equivalent body shapes, after inducing a lesion site, one of the mice 12, administered with the fluorescent marking agent of a fluorescent substance held by an antibody that specifically attaches to the lesion site, can be employed as the sample mouse 12A, and the other of the mice 12, administered with the fluorescent substance not specifically attaching to the specific site, such as, for example, a lesion site, can be employed as the control mouse 12B.

In such cases, the mouse 12 employed as the control mouse 12B is administered with the fluorescent substance, loaded into the optical measurement device 14 at a timing in a case in which the fluorescent substance has dispersed within the body, and measurement data Dr (x, θ, m) is acquired. After the mouse 12 employed as the sample mouse 12A is administered with the fluorescent marking agent, it is loaded into the optical measurement device 14 at a timing for attaching the fluorescent marking agent to the specific site, and the measurement data Ds (x, θ, m) is acquired.

By using the measurement data Dr (x, θ, m) acquired in this manner, corrected measurement data DS (x, θ, m) is obtained in which the influence of fluorescent light generated from fluorescent substance dispersed within the body of the sample mouse 12A is suppressed. Consequently, reconstruction of high resolution optical tomographic images of the specific site can be performed.

However, while explanation has been given above of a case in which a control mouse 12B different from the sample mouse 12A is employed, there is no limitation thereto. For example, before employing the mouse 12 as the sample mouse 12A, the same mouse 12 may be employed as the control mouse 12B so as to acquire the measurement data Dr (x, θ, m).

Namely, prior to inducing the lesion site, such as, for example, by injecting the diseased cells into the mouse 12, this mouse 12 may be employed as the control mouse 12B, and measurement data Dr (x, θ, m) acquired. Then, the lesion site is induced, such as, for example, by injecting diseased cells into the mouse 12. Then, the fluorescent substance (fluorescent marking agent) may be administered to this mouse 12, and the measurement data Ds (x, θ, m) acquired with this mouse 12 as the sample mouse 12A at a timing in a case in which the administered fluorescent substance has attached to the lesion site.

In a case in which different mice 12 are employed for the sample mouse 12A and the control mouse 12B, since specific fluorescent light peculiar to the individual mouse 12 is present, it is difficult to remove the individual-specific fluorescent light. In order to remove the individual-specific fluorescent light, the same mouse 12 may be employed as the sample mouse 12A and the control mouse 12B, thereby enabling the individual-specific fluorescent light to be removed.

In such cases, the lesion site may be induced in the mouse 12. In such cases, prior to administering the antibody including the fluorescent substance (fluorescent marking agent), the fluorescent substance alone is administered, and the measurement data Dr (x, θ, m) is acquired. Then the fluorescent marking agent is administered to acquire the measurement data Ds (x, θ, m). It is thereby possible to remove the unwanted light components including the individual-specific fluorescent light of the mouse 12. Note that the timing for administering the fluorescent marking agent to the mouse 12 is preferably after the first administered fluorescent substance has been excreted from the body, and should at least be after a duration such that the fluorescent marking agent has been expelled from the body by the time the fluorescent marking agent attaches to the specific site.

Further, in a case in which the antibody containing the fluorescent substance is administered to the mouse 12, the antibody containing the fluorescent substance circulates within the body and disperses, and then the fluorescent substance progressively attaches to the lesion site. Consequently, there is a significant duration that elapses before the mouse 12 is employed as the sample mouse 12A, and this duration may be utilized as a standardization sample.

In a case of doing so, after administering the antibody containing the fluorescent substance as the fluorescent marking agent to the mouse 12, first, in a case in which the fluorescent marking agent is in a dispersed state within the body, the measurement data Dr (x, θ, m) use in the standardization sample are acquired. Then, at a timing in a case in which the fluorescent marking agent has attached to the lesion site, measurement data Ds (x, θ, m) is acquired for this mouse 12 as the sample mouse 12A, a test sample.

In such cases too, by employing the same mouse 12 as the sample mouse 12A, and also as the control mouse 12B as the standardization sample, removal of unwanted light generated by individual-specific fluorescent light for each individual mouse 12 is enabled.

However, there is no need to use the same living organism for the standardization sample as for the sample mouse 12A if the aim is only to remove the unwanted light component caused by the device. Namely, a substance (anisotropic scattering medium) having equivalent optical properties (for example, light transmission scattering coefficient $\mu'$ or the like) to those of the mouse 12 for the sample mouse 12A may be employed, a model of the mouse 12 (referred to below as a phantom mouse) prepared, with the phantom mouse accommodated in the sample holder 30 and used as the standardization sample.

As such a phantom mouse, for example, preferably a substance that does not generate fluorescent light due to the excitation light to be generated from the light source head 58 is employed, and preferably a substance having a uniform surface reflectivity to the excitation light is employed. Further, preferably the surface state, including the surface reflectivity, is a surface state equivalent to that of the sample mouse 12A.

By employing such a phantom mouse, a correction coefficient α is obtained, from the measurement data Dr (x, θ, m) of the phantom mouse and the measurement data Ds (x, θ, m) of the mouse 12, from which at least the unwanted light component caused by the device is removed. Namely, influence on the light received by the light receiving heads 60 (60A to 60K) due to, for example, different diffusion of the excitation light or the fluorescent light to that of the mouse 12, is prevented.

In this manner, in the optical tomography measurement system 10, measurement data Ds (x, θ, m) is not simply acquired with the sample mouse 12A as the test sample, and reconstruction of optical tomographic images performed based on this measurement data Ds (x, θ, m). Instead, measurement data Dr (x, θ, m) is acquired in advance employing a standardization sample under predetermined conditions, a correction coefficient α is set using the measurement data Dr (x, θ, m) and the measurement data Ds (x, θ, m), and this correction coefficient α is used to generate corrected measurement data DS (x, θ, m) as the measurement data for appropriate application to reconstruction of optical tomographic images.

By so doing, since measurement data is obtained in which an unwanted light component received by the light receiving head 60 is suppressed from the measurement data, appropriate optical tomographic image reconstruction for the test sample is enabled.

Note that there is no limitation to the configurations explained in the present exemplary embodiment above. For example, in the present exemplary embodiment, configuration is made in which the corrected measurement data is generated by the data processing device 16, however, there is no limitation thereto, and configuration may be made such that the corrected measurement data is generated by the optical measurement device 14, and this corrected measurement data is output.

Further, while explanation is given in the present exemplary embodiment above of an example where the mouse 12 is used as the test sample, the optical tomography measurement system according to the present exemplary embodiment can be employed with any living organism as the measurement subject.

Furthermore, the present invention is not limited to the optical tomography measurement system 10, and appropriate application can be made to any configuration of optical tomographic measurement device in which excitation light is illuminated onto a test sample, light emitted from the test sample is detected, and tomographic images based on the intensity of this light are reconstructed.

In order to achieve the above object, in a case in which a living organism is employed as a test sample and fluorescent light generated by excitation light from a fluorescent substance administered to the test sample is received by a light receiving component at plural locations around the periphery of the test sample in a flat plane passing through an observation site of the test sample, a measurement data correction method of the present invention is employed for reconstruction of an optical tomographic image of the test sample along the flat plane passing through the observation site. The measurement data correction method includes: acquiring first measurement data that is measurement data in a flat plane passing through the observation site and acquiring second measurement data that is measurement data in a flat plane passing through a site of interest of the test sample different from the observation site; using a predetermined standardization sample for the test sample to acquire first standardization measurement data that is measurement data in a flat plane corresponding to the flat plane of the observation site, and to acquire second standardization measurement data that is measurement data corresponding to a flat plane of the site of interest; using the second measurement data and the second standardization measurement data corresponding to the site of interest of the test sample, and setting a correction coefficient such that the second standardization measurement data is cancelled out by the second measurement data; and generating corrected measurement data, as measurement data to be used in reconstruction of an optical tomographic image along the flat plane passing through the observation site of the test sample, from the first measurement data and the first standardization measurement data using the correction coefficient.

Further, for a living organism employed as a test sample with fluorescent light being generated by excitation light from a fluorescent substance administered to the test sample, an optical tomography measurement device of the present invention performs reconstruction, from measurement data obtained from receiving light with a light receiving component at plural locations around the periphery of the test sample in a flat plane passing through an observation site of the test sample, of an optical tomographic image of the test sample along the flat plane passing through the observation site. The device includes: a first acquiring component that acquires with the light receiving component first measurement data that is measurement data in a flat plane passing through the observation site and second measurement data that is measurement data in a flat plane passing through a site of interest of the test sample different from the observation site; a second acquiring component that uses a predetermined standardization sample for the test sample to acquire with the light receiving component first standardization measurement data that is measurement data in a flat plane corresponding to the flat plane including the observation site, and to acquire second standardization measurement data that is measurement data corresponding to a flat plane including the site of interest; a correction coefficient setting component that uses the second measurement data and the second standardization measurement data corresponding to the site of interest of the test sample, and sets a correction coefficient such that the second standardization measurement data is cancelled out by the second measurement data; and a correction component that generates corrected measurement data, of measurement data to be used in reconstruction of an optical tomographic image along the flat plane passing through the observation site of the test sample, from the first measurement data and the first standardization measurement data using the correction coefficient.

Furthermore, for a living organism employed as a test sample with fluorescent light being generated by excitation light from a fluorescent substance administered to the test sample, a storage medium readable by a computer of the present invention is a storage medium storing a program of instructions executable by the computer, functioning the computer as components, the computer provided to an optical tomography measurement device performing reconstruction, from measurement data obtained by a light receiving component receiving light at plural locations around the periphery of the test sample in a flat plane passing through an observation site of the test sample, of an optical tomographic image of the test sample along the flat plane passing through the observation site. The components including: a first acquiring component that acquires with the light receiving component first measurement data that is measurement data in a flat plane passing through the observation site and second measurement data that is measurement data in a flat plane passing through a site of interest of the test sample different from the observation site; a second acquiring component that uses a predetermined standardization sample for the test sample to acquire with the light receiving component first standardization measurement data that is measurement data in a flat plane corresponding to the flat plane including the observation site, and second standardization measurement data that is measurement data corresponding to a flat plane including the site of interest; a correction coefficient setting component that uses the second measurement data and the second standardization measurement data corresponding to the site of interest of the test sample, and sets a correction coefficient such that the second standardization measurement data is cancelled out by the second measurement data; and a correction component that generates corrected measurement data, of measurement data to be used in reconstruction of an optical tomographic image along the flat plane passing through the observation site of the test sample, from the first measurement data and the first standardization measurement data using the correction coefficient.

In the present invention configured as described above, a living organism of predetermined conditions is used as the standardization sample for the test sample, and measurement data of the test sample is acquired and measurement data of the standardization sample is acquired as standardization measurement data.

In a case in which the measurement data and the standardization measurement data has been acquired, from second measurement data that is measurement data of the site of interest on the test sample, and second measurement data that is measurement data of the standardization sample corresponding to the site of interest, the correction coefficient is set such that the second standardization measurement data is cancelled out by the second measurement data.

Then, corrected measurement data is generated, as measurement data to be used in reconstruction of a optical tomographic image including the observation site of the test sample, from the correction coefficient, and the first measurement data corresponding to the observation site and the second standardization measurement data. In a case of doing so, since the correction coefficient is set such that the first standardization measurement data is cancelled out by the first measurement data, corrected measurement data is obtained from which an unwanted light component generated in a case of measuring the standardization sample and the test sample, respectively, has been removed.

Consequently, reconstruction of an optical tomographic image of the fluorescent light on the test sample differing from that of the standardization sample becomes possible.

In the present invention such as this, the first measurement data may be acquired by administering to the test sample as the fluorescent substance, a fluorescent marker agent that specifically attaches to a specific site in the body and generates fluorescent light, with the specific site as the observation site.

In a case of doing so, in the present invention, the standardization sample may be a living organism syngeneic to the test sample, and may be a living organism to which the fluorescent substance is administered in a state in which attachment to the specific site is suppressed, or the test sample prior to being administered with the fluorescent marker agent may be employed as the standardization sample.

Further, in the present invention, the test sample to which the fluorescent marker agent has been administered may be employed as the standardization sample at a timing in a case in which the fluorescent marker agent is dispersed in the body, and prior to attachment to the specific site.

Furthermore, in the present invention, the standardization sample may be a model of the test sample in a substance that does not generate fluorescent light with the excitation light, and with a surface state to light matched to the surface state to light of the test sample. In a case of configuring in this manner, the optical characteristics including an absorption coefficient to light of the model may be matched to optical characteristics including an absorption coefficient to light of the test sample.

Further, in the present invention, the fluorescent substance that disperses in the body of the test sample without attaching to the specific site and generates fluorescent light may be administered to the test sample as the standardization sample.

Further, in the optical tomography measurement device applied in the present invention, a selection component may be included that selects the site of interest in the test sample, wherein: the first acquiring component acquires measurement data along a flat plane including the observation site of the test sample, and along plural flat planes that are respectively parallel to the flat plane including the observation site and pass through the test sample; the second acquiring component acquires correction measurement data along flat planes corresponding to each of the respective plural flat planes acquired by the first acquiring component; and the correction coefficient setting component sets the correction coefficient with measurement data and correction measurement data corresponding to a flat plane including the site of interest selected by the selection component as the second measurement data and the second correction measurement data.

According to the present invention as explained above, first and second measurement data is acquired as measurement data of the test sample, and first and second standardization measurement data is acquired as measurement data using the standardization sample, and the correction coefficient is set such that the second standardization measurement data is cancelled out by the second measurement data corresponding to the site of interest. Based on this correction coefficient, corrected measurement data is generated from the first measurement data and the first standardization measurement data corresponding to the observation site that is the site for reconstruction of the optical tomographic image.

By so doing, the measurement data (corrected measurement data) is obtained from which unwanted light has been removed, and an effect is obtained in that an appropriate optical tomographic image is reconstructed using this measurement data.

What is claimed is:

1. A measurement data correction method, wherein,
a living organism is employed as a test sample, fluorescent light generated by excitation light from a fluorescent substance administered to the test sample is received by a light receiving component at a plurality of locations around the periphery of the test sample in a flat plane passing through an observation site of the test sample, and the method is employed for reconstruction of an optical tomographic image of the test sample along the flat plane passing through the observation site,
the method comprising:
acquiring first measurement data that is measurement data in a flat plane passing through the observation site and acquiring second measurement data that is measurement data in a flat plane passing through a site of interest of the test sample different from the observation site;
using a predetermined standardization sample for the test sample to acquire first standardization measurement data that is measurement data in a flat plane corresponding to the flat plane of the observation site, and to acquire second standardization measurement data that is measurement data corresponding to a flat plane of the site of interest;
using the second measurement data and the second standardization measurement data corresponding to the site of interest of the test sample, and setting a correction coefficient such that the second standardization measurement data is cancelled out by the second measurement data; and
generating corrected measurement data, as measurement data to be used in reconstruction of an optical tomographic image along the flat plane passing through the observation site of the test sample, from the first measurement data and the first standardization measurement data using the correction coefficient.

2. The measurement data correction method of claim 1, wherein the first measurement data is acquired by administering as the fluorescent substance a fluorescent marker agent that specifically attaches to a specific site in the body and generates fluorescent light, with the specific site as the observation site.

3. The measurement data correction method of claim 2, wherein the standardization sample is a living organism syngeneic to the test sample, and is a living organism to which the fluorescent substance is administered in a state in which attachment to the specific site is suppressed.

4. The measurement data correction method of claim 2, wherein the test sample prior to administering the fluorescent marker agent is employed as the standardization sample.

5. The measurement data correction method of claim 2, wherein the test sample to which the fluorescent marker agent has been administered is employed as the standardization sample at a timing in a case in which the fluorescent marker agent is dispersed in the body, and prior to attachment to the specific site.

6. The measurement data correction method of claim 2, wherein the standardization sample is a model of the test sample in a substance that does not generate fluorescent light with the excitation light, and with a surface state to light matched to the surface state to light of the test sample.

7. The measurement data correction method of claim 6, wherein optical characteristics including an absorption coefficient to light of the model are matched to optical characteristics including an absorption coefficient to light of the test sample.

8. The measurement data correction method of claim 2, wherein the fluorescent substance that disperses in the body of the test sample without attaching to the specific site and generates fluorescent light is administered to the test sample as the standardization sample.

9. An optical tomography measurement device, wherein,
a living organism is employed as a test sample, fluorescent light is generated by excitation light from a fluorescent substance administered to the test sample, and the device performs reconstruction, from measurement data obtained from receiving light with a light receiving component at a plurality of locations around the periphery of the test sample in a flat plane passing through an observation site of the test sample, of an optical tomographic image of the test sample along the flat plane passing through the observation site, the device comprising:
a first acquiring component that acquires with the light receiving component first measurement data that is measurement data in a flat plane passing through the observation site and second measurement data that is measurement data in a flat plane passing through a site of interest of the test sample different from the observation site;
a second acquiring component that uses a predetermined standardization sample for the test sample to acquire with the light receiving component first standardization measurement data that is measurement data in a flat plane corresponding to the flat plane including the observation site, and to acquire second standardization measurement data that is measurement data corresponding to a flat plane including the site of interest;
a correction coefficient setting component that uses the second measurement data and the second standardization measurement data corresponding to the site of interest of the test sample, and sets a correction coefficient such that the second standardization measurement data is cancelled out by the second measurement data; and
a correction component that generates corrected measurement data, of measurement data to be used in reconstruction of an optical tomographic image along the flat plane passing through the observation site of the test sample, from the first measurement data and the first standardization measurement data using the correction coefficient.

10. The optical tomography measurement device of claim 9, further comprising a selection component that selects the site of interest in the test sample, wherein:
the first acquiring component acquires measurement data along a flat plane including the observation site of the test sample, and along a plurality of flat planes that are respectively parallel to the flat plane including the observation site and pass through the test sample;

the second acquiring component acquires correction measurement data along flat planes corresponding to each of the respective plurality of flat planes acquired by the first acquiring component; and the correction coefficient setting component sets the correction coefficient with measurement data and correction measurement data corresponding to a flat plane including the site of interest selected by the selection component as the second measurement data and the second correction measurement data.

11. A non-transitory storage medium readable by a computer, the storage medium storing a program of instructions executable by the computer to function the computer, for a living organism employed as a test sample, fluorescent light generated by excitation light from a fluorescent substance administered to the test sample being received by a light receiving component at a plurality of locations around the periphery of the test sample in a flat plane passing through an observation site of the test sample, functioning the computer as components for performing reconstruction of an optical tomographic image of the test sample along the flat plane passing through the observation site from measurement data obtained by the light receiving component, the components comprising:

a first acquiring component that acquires with the light receiving component first measurement data that is measurement data in a flat plane passing through the observation site and second measurement data that is measurement data in a flat plane passing through a site of interest of the test sample different from the observation site;

a second acquiring component that uses a predetermined standardization sample for the test sample to acquire with the light receiving component first standardization measurement data that is measurement data in a flat plane corresponding to the flat plane including the observation site, and second standardization measurement data that is measurement data corresponding to a flat plane including the site of interest;

a correction coefficient setting component that uses the second measurement data and the second standardization measurement data corresponding to the site of interest of the test sample, and sets a correction coefficient such that the second standardization measurement data is cancelled out by the second measurement data; and a correction component that generates corrected measurement data, of measurement data to be used in reconstruction of an optical tomographic image along the flat plane passing through the observation site of the test sample, from the first measurement data and the first standardization measurement data using the correction coefficient.

12. The non-transitory storage medium of claim 11, the components further comprising a selection component that selects the site of interest in the test sample, wherein:

the first acquiring component acquires measurement data along a flat plane including the observation site of the test sample, and along a plurality of flat planes that are respectively parallel to the flat plane including the observation site and pass through the test sample;

the second acquiring component acquires correction measurement data along flat planes corresponding to each of the respective plurality of flat planes acquired by the first acquiring component; and the correction coefficient setting component sets the correction coefficient with measurement data and correction measurement data corresponding to a flat plane including the site of interest selected by the selection component as the second measurement data and the second correction measurement data.

* * * * *